United States Patent
Weeber et al.

(10) Patent No.: US 9,241,975 B2
(45) Date of Patent: Jan. 26, 2016

(54) REELIN RESCUES CONGNITIVE FUNCTION

(75) Inventors: Edwin Weeber, Apollo Beach, FL (US);
Lisa Zhao, Alhambra, CA (US);
Melinda Peters, Riverview, FL (US)

(73) Assignees: University of South Florida, Tampa, FL (US); Vanderbilt University, Nashville, TN (US)

( * ) Notice: Subject to any disclaimer, the term of this patent is extended or adjusted under 35 U.S.C. 154(b) by 0 days.

(21) Appl. No.: 13/206,174

(22) Filed: Aug. 9, 2011

(65) Prior Publication Data
US 2012/0058109 A1    Mar. 8, 2012

Related U.S. Application Data

(63) Continuation of application No. PCT/US2010/023615, filed on Feb. 9, 2010.

(60) Provisional application No. 61/150,890, filed on Feb. 9, 2009.

(51) Int. Cl.
| | |
|---|---|
| *A61K 39/395* | (2006.01) |
| *A61K 39/40* | (2006.01) |
| *A61K 39/42* | (2006.01) |
| *A61K 38/17* | (2006.01) |
| *A61K 38/53* | (2006.01) |

(52) U.S. Cl.
CPC .............. *A61K 38/1709* (2013.01); *A61K 38/53* (2013.01)

(58) Field of Classification Search
None
See application file for complete search history.

(56) References Cited

U.S. PATENT DOCUMENTS

| | | | |
|---|---|---|---|
| 6,323,177 B1 | 11/2001 | Curran et al. | |
| 7,341,844 B2 | 3/2008 | Fatemi | |
| 2003/0165485 A1 | 9/2003 | Bertilsson et al. | |

OTHER PUBLICATIONS

Hiesberger et al., Direct Binding of Reelin to VLDL Receptor and ApoE Receptor 2 Induces Tyrosine Phosphorylation of Disabled-1 and Modulates Tau Phosphorylation, Neuron, 199, vol. 24, pp. 481-489.
Qiu et al., Cognitive Disruption and Altered Hippocampus Synaptic Function in Reelin Haploinsufficient Mice, Neurobiology of Learning and Memory, 2006, vol. 85, pp. 228-242.
Krueger et al., Assessment of Cognitive Function in the Heterozygous Reeler Mouse, Psychopharmacology, 2006, vol. 189, pp. 95-104.
Utsunomiya-Tate et al., Reelin Molecules Assemble Together to Form a Large Protein Complex, Which is Inhibited by the Function-Blocking CR-50 Antibody, PNAS, 2000, vol. 97, No. 17, pp. 9729-9734.
Moskovitz et al., Selenium-Deficient Diet Enhances Protein Oxidation and Affects Methionine Sulfoxide Reductase (MsrB) Protein Level in Certain Mouse Tissues, PNAS, 2003, vol. 100, No. 13, pp. 7486-7490.
Yang et al., Activated Protein C Ligation of ApoER2 (LRP8) Causes Dab1-dependent Signaling in U937 Cells, PNAS, 2009, vol. 106, No. 1, pp. 274-279.
Liu et al., Down-Regulation of Dendritic Spine and Glutamic Acid Decarboxylase 67 Expressions in the Reelin Haploinsufficient Heterozygous Reeler Mouse, PNAS, 2001, vol. 98, No. 6, pp. 3477-3482.
Huang et al., Mice Lacking the Gene Encoding Tissue-Type Plasminogen Activator Show a Selective Interference with Late-Phase Long-Term Potentiation in Both Schaffer Collateral and Mossy Fiber Pathways, PNAS, 1996, vol. 93, pp. 8699-8704.
Jacobsen et al., Early-Onset Behavioral and Synaptic Deficits in a Mouse Model of Alzheimer's Disease, PNAS, 2006, vol. 103, No. 13, pp. 5161-5166.
Schmechel et al., Increased Amyloid Beta-peptide Deposition in Cerebral Cortex as a Consequence of Apolipoprotein E Genotype in Late-Onset Alzheimer Disease, PNAS, 1993, vol. 90, pp. 9649-9653.
Dong et al., Reelin and Glutamic Acid Decarboxylase67 Promoter Remodeling in an Epigenetic Methionine-Induced Mouse Model of Schizophrenia, PNAS, 2005, vol. 102, No. 35, pp. 12578-12583.
Impagnatiello et al., A Decrease of Reelin Expression as a Putative Vulnerability Factor in Schizophrenia, PNAS, 1998, vol. 95, pp. 15718-15723.
Nakajima et al., Disruption of Hippocampal Development in vivo by CR-50 mAb Against Reelin, PNAS, 1997, vol. 94, No. 15, pp. 8196-8201.
Hill et al., Conserved Nucleotide Sequences in the Open Reading Frame and 3' Untranslated Region of Selenoprotein P mRNA, PNAS, 1993, vol. 90, No. 2, pp. 537-541.
Pesold et al., Reelin is Preferentially Expressed in Neurons Synthesizing Gamma-Aminobutyric Acid in Cortex and Hippocampus of Adult Rats, PNAS, 1998, vol. 95, No. 6, pp. 3221-3226.
Forster et al., Reelin, Disabled 1, and beta1 Integrins are Required for the Formation of the Radial Glial Scaffold in the Hippocampus, PNAS, 2002, vol. 99, No. 20, pp. 13178-13183.
Jossin et al., Reelin Signals through Phosphatidylinositol 3-Kinase and Akt to Control Cortical Development and through mTor to Regulate Dendritic Growth, Molecular and Cellular Biology, 2007, vol. 27, No. 20, pp. 7113-7124.
Yasuda et al., The JIP Group of Mitogen-Activated Protein Kinase Scaffold Proteins, Molecular and Cellular Biology, 1999, vol. 19, No. 10, pp. 7245-7254.
Strasser et al., Receptor Clustering is Involved in Reelin Signaling, Molecular and Cellular Biology, 2004, vol. 24, No. 3, pp. 1378-1386.
Quinlan et al., A Molecular Mechanism for Stabilization of Learning-Induced Synaptic Modifications, Neuron, 2004, vol. 41, pp. 185-192.
Barria et al., NMDA Receptor Subunit Composition Controls Synaptic Plasticity by Regulating Binding to CaMKII, Neuron, 2005, vol. 48, pp. 289-301.

(Continued)

*Primary Examiner* — Olga N Chernyshev
(74) *Attorney, Agent, or Firm* — Robert J. Varkonyi; Smith & Hopen, P.A.

(57) ABSTRACT

Disclosed are methods of influencing, and enhancing, cognitive function by increasing, and/or preventing interference with, Reelin levels as well as Reelin signaling. Cognitive function is improved, in a subject in need thereof, by administering a therapeutically effective amount of Reelin, a Reelin-specific modulator or an agonist of a lipoprotein receptor to the subject. The lipoprotein receptor can be selected from candidates such as ApoER2 and VLDLR. As disclosed herein, agonists of the lipoprotein receptor for use with the inventive method include APC, Sep and Fc-RAP. In addition to administering exogenous Reelin, a Reelin-specific modulator, such as a recombinant Reelin fragment, can be used to increase Reelin levels and/or signaling.

2 Claims, 23 Drawing Sheets

(56) References Cited

OTHER PUBLICATIONS

Guo et al., Activated Protein C Prevents Neuronal Apoptosis via Protease Activated Receptors 1 and 3, Neuron, 2004, vol. 41, pp. 563-572.

D'Arcangelo et al., Reelin is a Ligand for Lipoprotein Receptors, Neuron, 1999, vol. 24, pp. 471-479.

Baranes et al., Tissue Plasminogen Activator Contributes to the Late Phase of LTP and to Synaptic Growth in the Hippocampal Mossy Fiber Pathway, Neuron, 1998, vol. 21, pp. 813-825.

Weeber et al., Reelin and ApoE Receptors Cooperate to Enhance Hippocampal Synaptic Plasticity and Learning, The Journal of Biological Chemistry, 2002, vol. 277, No. 42, pp. 39944-39952.

Gotthardt et al., Interactions of the Low Density Lipoprotein Receptor Gene Family with Cytosolic Adaptor and Scaffold Proteins Suggest Diverse Biological Functions in Cellular Communication and Signal Transduction, The Journal of Biological Chemistry, 2000, vol. 275, No. 33, pp. 25616-25624.

Hoe et al., Apolipoprotein E Receptor 2 Interactions with the N-Methyl-D-aspartate Receptor, The Journal of Biological Chemistry, 2006, vol. 281, No. 6, pp. 3425-3431.

Hoe et al., DAB1 and Reelin Effects on Amyloid Precursor Protein and ApoE Receptor 2 Trafficking and Processing, The Journal of Biological Chemistry, 2006, vol. 281, No. 46, pp. 35176-35185.

Herz et al., 39-kDa Protein Modulates Binding of Ligands to Low Density Lipoprotein Receptor-related Protein/alpha2-Macroglobulin Receptor, The Journal of Biological Chemistry, 1991, vol. 266, No. 31, pp. 21232-21238.

Qiu et al., Alpha2-Macroglobulin Exposure Reduces Calcium Responses to N-Methyl-D-Aspartate via Low Density Lipoprotein Receptor-related Protein in Cultured Hippocampal Neurons, The Journal of Biological Chemistry, 2002, vol. 277, No. 17, pp. 14458-14466.

Keshvara et al., Identification of Reelin-induced Sites of Tyrosyl Phosphorylation on Disabled 1, The Journal of Biological Chemistry, 2001, vol. 276, No. 19, pp. 16008-16014.

Barnes et al., Tyrosine-phosphorylated Low Density Lipoprotein Receptor-related Protein 1 (LRP1) Associates with the Adaptor Protein SHC in SRC-transformed Cells, The Journal of Biological Chemistry, 2001, vol. 276, No. 22, pp. 19119-19125.

Morimura et al., Disabled1 Regulates the Intracellular Trafficking of Reelin Receptors, The Journal of Biological Chemistry, 2005, vol. 280, No. 17, pp. 16901-16908.

Mosnier et al., Activated Protein C Mutant with Minimal Anticoagulant Activity, Normal Cytoprotective Activity, and Preservation of Thrombin Activable Fibrinolysis Inhibitor-dependent Cytoprotective Functions, The Journal of Biological Chemistry, 2007, vol. 282, No. 45, pp. 33022-33033.

Kang et al., Presenilins Mediate Phosphatidylinositol 3-Kinase/AKT and ERK Activation via Select Signaling Receptors, The Journal of Biological Chemistry, 2005, vol. 280, No. 36, pp. 31537-31547.

Stine et al., In Vitro Characterization of Conditions for Amyloid-Beta Peptide Oligomerization and Fibrillogenesis, The Journal of Biological Chemistry, 2003, vol. 278, No. 13, pp. 11612-11622.

Gale et al., Molecular Characterization of an Extended Binding Site for Coagulation Factor Va in the Positive Exosite of Activated Protein C, The Journal of Biological Chemistry, 2002, vol. 277, No. 32, pp. 28836-28840.

Read et al., Selenium and Amino Acid Composition of Selenoprotein P, the Major Selenoprotein in Rat Serum, The Journal of Biological Chemistry, 1990, vol. 265, No. 29, pp. 17899-17905.

Gu et al., Impaired Conditioned Fear and Enhanced Long-term Potentiation in Fmr2 Knock-out Mice. Journal of Neuroscience, 2002, vol. 22, No. 7, pp. 2753-2763.

Hoareau et al., Amyloid Precursor Protein Cytoplasmic Domain Antagonizes Reelin Neurite Outgrowth Inhibition of Hippocampal Neurons, Neurobiol Aging, 2008, vol. 29, pp. 542-553.

Isermann et al., Activated Protein C Protects Against Diabetic Nephropathy by Inhibiting Endothelial and Podocyte Apoptosis, Nat. Med., 2007, vol. 13, No. 11, pp. 1349-1358.

Mosnier et al., Activated Protein C Variants with Normal Cytoprotective but Reduced Anticoagulant Activity, Blood, 2004, vol. 104, pp. 1740-1744.

Massey et al., Differential Roles of NR2A and NR2B-Containing NMDA Receptors in Cortical Long-term Potentiation and Long-term Depression, J. Neurosci., 2004, vol. 24, No. 36, pp. 7821-7828.

Chavis et al., Integrins Mediate Functional Pre- and Postsynaptic Maturation at a Hippocampal Synapse, Nature, 2001, vol. 411, pp. 317-321.

Liu et al., Role of NMDA Receptor Subtypes in Governing the Direction of Hippocampal Synaptic Plasticity, Science, 2004, vol. 304, pp. 1021-1024.

Zhuo et al., Role of Tissue Plasminogen Activator Receptor LRP in Hippocampal Long-term Potentiation, J Neurosci, 2000, vol. 20, No. 2, pp. 542-549.

Morgan et al., Electrical Stimuli Patterned After the Theta-rhythm Induce Multiple Forms of LTP, J Neurophysiol., 2001, vol. 86, pp. 1289-1296.

Nagy et al., Matrix Metalloproteinase-9 is Required for Hippocampal Late-phase Long-term Potentiation and Memory, J Neurosci, 2006, vol. 26, No. 7, pp. 1923-1934.

Mitchell et al., X11 beta Rescues Memory and Long-term Potentiation Deficits in Alzheimer's Disease APPswe Tg2576 Mice, Hum Mol Genet, 2009, vol. 18, No. 23, pp. 4492-4500.

Beffert, U., A. Durudas, et al. (2006). "Functional dissection of Reelin signaling by site-directed disruption of Disabled-1 adaptor binding to apolipoprotein E receptor 2: distinct roles in development and synaptic plasticity." J Neurosci 26(7): 2041-52.

Beffert, U., E. J. Weeber, et al. (2005). "Modulation of synaptic plasticity and memory by Reelin involves differential splicing of the lipoprotein receptor Apoer2." Neuron 47(4): 567-79.

Beffert, U., E. J. Weeber, et al. (2004). "Reelin and cyclin-dependent kinase 5-dependent signals cooperate in regulating neuronal migration and synaptic transmission." J Neurosci 24(8): 1897-1906.

Berlau, D. J. and J. L. McGaugh (2006). "Enhancement of extinction memory consolidation: The role of the noradrenergic and GABAergic systems within the basolateral amygdala." Neurobiol Learn Mem. 86: 123-132.

Bu, G. and A. L. Schwartz (1998). "RAP, a novel type of ER chaperone." Trends Cell Biol 8(7): 272-6.

Costa, E., J. Davis, et al. (2002). "The heterozygote reeler mouse as a model for the development of a new generation of antipsychotics." Curr Opin Pharmacol 2(1): 56-62.

D'Arcangelo, G. (2006). "Reelin mouse mutants as models of cortical development disorders." Epilepsy Behav 8(1): 81-90.

Del Rio, J. A., B. Heimrich, et al. (1997). "A role for Cajal-Retzius cells and reelin in the development of hippocampal connections." Nature 385(6611): 70-4.

Drakew, A., M. Frotscher, et al. (1998). "Developmental distribution of a reeler gene-related antigen in the rat hippocampal formation visualized by CR-50 immunocytochemistry." Neuroscience 82(4): 1079-86.

Fatemi, S. H. (2005). "Reelin glycoprotein: structure, biology and roles in health and disease." Mol Psychiatry 10(3): 251-7.

Guidotti, A., J. Auta, et al. (2000). "Decrease in reelin and glutamic acid decarboxylase67 (GAD67) expression in schizophrenia and bipolar disorder: a postmortem brain study." Arch Gen Psychiatry 57(11): 1061-9.

Guidotti, A., J. Auta, et al. (2005). "GABAergic dysfunction in schizophrenia: new treatment strategies on the horizon." Psychopharmacology (Berl) 180(2): 191-205.

Mosnier LO, Zlokovic BV, Griffin JH. (2007) The cytoprotective protein C pathway. Blood 109:3161-3172.

Kuo, G., L. Arnaud, et al. (2005). "Absence of Fyn and Src causes a reeler-like phenotype." J Neurosci 25(37): 8578-86.

McIlwain, K. L., M. Y. Merriweather, et al. (2001). "The use of behavioral test batteries: effects of training history." Physiol Behav 73(5): 705-17.

Qiu, S. K. M. Korwek, et al. (2006). "A fresh look at an ancient receptor family: emerging roles for low density lipoprotein receptors in synaptic plasticity and memory formation." Neurobiol Learn Mem 85(1): 16-29.

(56) References Cited

OTHER PUBLICATIONS

Arendash GW, King DL, Gordon MN, et al. (2001) Progressive, age-related behavioral impairments in transgenic mice carrying both mutant amyloid precursor protein and presenilin-1 transgenes. Brain Res 891:42-53.

Yabut, O., A. Renfro, et al. (2007). "Abnormal laminar position and dendrite development of interneurons in the reeler forebrain." Brain Res. 1140: 75-83.

Yamada, M., T. Chiba, et al. (2005). "Implanted cannula-mediated repetitive administration of Abeta25-35 into the mouse cerebral ventricle effectively impairs spatial working memory." Behav Brain Res 164(2): 139-46.

Tueting, P., E. Costa, et al. (1999). "The phenotypic characteristics of heterozygous reeler mouse." Neuroreport 10(6): 1329-34.

Alcantara S, Ruiz M, D'Arcangelo G, et al. (1998) Regional and cellular patterns of reelin mRNA expression in the forebrain of the developing and adult mouse. J Neuroscience 18(19):7779-7799.

Qiu S, Weeber EJ. (2007) Reelin signaling facilitates maturation of CA1 glutamatergic synapses. J Neurophysiol 97:2312-2321.

Qiu S, Li L, Weeber EJ, May JM. (2007) Ascorbate transport by primary cultured neurons and its role in neuronal function and protection against excitotoxicity. J Neurosci Res 85:1046-1056.

Leighty RE, Nilsson LN, Potter H, et al. (2004) Use of multimetric statistical analysis to characterize and discriminate between the performance of four Alzheimer's transgenic mouse lines differing in Abeta deposition. Behav Brain Res 153:107-121.

Arendash GW, Gordon MN, Diamond DM, et al. (2001) Behavioral assessment of Alzheimer's transgenic mice following long-term Abeta vaccination: task specificity and correlations between Abeta deposition and spatial memory. DNA Cell Biol 20(11):737-744.

Zacharko, R. M., G. MacNeil, et al. (1999). "Proactive influence of a surgical stressor on locomotor activity, exploration and anxiety-related behaviour following acute footshock in the mouse." Brain Res Bull 48(3): 283-90.

Lu W, Man H, Ju W, Trimble WS, MacDonald JF, Wang YT. (2001) Activation of synaptic NMDA receptors induces membrane insertion of new AMPA receptors and LTP in cultured hippocampal neurons. Neuron 29:243-254.

Pickard L, Noel J, Duckworth JK, et al. (2001) Transient synaptic activation of NMDA receptors leads to the insertion of native AMPA receptors at hippocampal neuronal plasma membranes. Neuropharmacology 41:700-713.

Harris EW, Ganong AH, Cotman CW. (1984) Long-term potentiation in the hippocampus involves activation of Nmethyl-D-aspartate receptors. Brain Res 323:132-137.

Frotscher M, Haas CA, Forster E. (2003) Reelin controls granule cell migration in the dentate gyrus by acting on the radial glial scaffold. Cereb Cortex 13:634-640.

Grosshans DR, Clayton DA, Coultrap SJ, Browning MD. (2002) LTP leads to rapid surface expression of NMDA but not AMPA receptors in adult rat CA1. Nat Neuroscie 5(1):27-33.

Barria A, Muller D, Derkach V, Griffith LC, Soderling TR. (1997) Regulatory phosphorylation of AMPA-type glutamate receptors by CaM-KII during long-term potentiation. Science 276:2042-2045.

Banke TG, Bowie D, Lee H, Huganir RL, Schousboe A, Traynelis SF. (2000) Control of GluR1 AMPA receptor function by cAMP-dependent protein kinase. J Neurosci 20(1):89-102.

Lee HK, Takamiya K, Han JS, et al. (2003) Phosphorylation of the AMPA receptor GluR1 subunit is required for synaptic plasticity and retention of spatial memory. Cell 112:631-643.

Hayashi Y, Shi SH, Esteban JA, Piccini A, Poncer JC, Malinow R. (2000) Driving AMPA receptors into synapses by LTP and CaMKII: requirement for GluR1 and PDZ domain interaction. Science 287:2262-2267.

Shi SH, Hayashi Y, Petralia RS, et al. (1999) Rapid spine delivery and redistribution of AMPA receptors after synaptic NMDA receptor activation. Science 284:1811-1816.

Chung HJ, Huang YH, Lau LF, Huganir RL. (2004) Regulation of the NMDA receptor complex and trafficking by activity-dependent phosphorylation of the NR2B subunit PDZ ligand. J Neurosci 24(45):10248-10259.

Chen Y, Beffert U, Ertunc M, et al. (2005) Reelin modulates NMDA receptor activity in cortical neurons. J Neurosci 25 (36):8209-8216.

Hayashi T, Huganir RL. Tyrosine phosphorylation and regulation of the AMPA receptor by SRC family tyrosine kinases. J Neurosci 2004;24(27):6152-6160.

Qiu S, Zhao LF, Korwek KM, Weeber EJ. (2006) Differential reelin-induced enhancement of NMDA and AMPA receptor activity in the adult hippocampus. J Neurosci 26(50):12943-12955.

Kaufmann WE, Moser HW. (2000) Dendritic anomalies in disorders associated with mental retardation. Cereb Cortex 10:981-991.

Weeber EJ, Jiang YH, Elgersma Y, et al. (2003) Derangements of hippocampal calcium/calmodulin-dependent protein kinase II in a mouse model for Angelman mental retardation syndrome. J Neurosci 23(7):2634-2644.

Irwin SA, Galvez R, Greenough WT. (2000) Dendritic spine structural anomalies in fragile-X mental retardation syndrome. Cereb Cortex 10:1038-1044.

Barnes AP, Milgram SL. (2002) Signals from the X: signal transduction and X-linked mental retardation. Int J Dev Neurosci 20:397-406.

Pappas GD, Kriho V, Pesold C. (2001) Reelin in the extracellular matrix and dendritic spines of the cortex and hippocampus: a comparison between wild type and heterozygous reeler mice by immunoelectron microscopy. J Neurocytol 30:413-425.

Sinagra M, Verrier D, Frankova D, et al. (2005) Reelin, very-low-density lipoprotein receptor, and apolipoprotein E receptor 2 control somatic NMDA receptor composition during hippocampal maturation in vitro. J Neurosci 25(26):6127-6136.

Lu YM, Roder JC, Davidow J, Salter MW. (1998) Src activation in the induction of long-term potentiation in CA1 hippocampal neurons. Science 279:1363-1367.

Salter MW, Kalia LV. (2004) Src kinases: a hub for NMDA receptor regulation. Nat Rev Neurosci 5:317-328.

Pramatarova A, Chen K, Howell BW. (2008) A genetic interaction between the APP and Dab1 genes influences brain development. Mol Cell Neurosci 37:178-186.

Schomburg L, Riese C, Michaelis M, et al. Synthesis and metabolism of thyroid hormones is preferentially maintained in selenium-deficient transgenic mice. Endocrinology 2006;147(3):1306-1313.

Hill KE, Zhou J, McMahan WJ, et al. Deletion of selenoprotein P alters distribution of selenium in the mouse. J Biol Chem 2003;278(16):13640-13646.

Hill KE, Zhou J, McMahan WJ, Motley AK, Burk RF. Neurological dysfunction occurs in mice with targeted deletion of the selenoprotein P gene. J Nutr 2004;134:157-161.

Trigona WL, Mullarky IK, Cao Y, Sordillo LM. Thioredoxin reductase regulates the induction of haem oxygenase-1 expression in aortic endothelial cells. Biochem J 2006;394:207-216.

Lei XG, Cheng WH. New roles for an old selenoenzyme: evidence from glutathione peroxidase-1 null and overexpressing mice. J Nutr 2005;135:2295-2298.

Schweizer U, Brauer AU, Kohrle J, Nitsch R, Savaskan NE. Selenium and brain function: a poorly recognized liaison. Brain Res Brain Res Rev 2004;45:164-178.

Kubo K, Mikoshiba K, Nakajima K. Secreted Reelin molecules form homodimers. Neurosci Res 2002;43:381-388.

Deane R, LaRue B, Sagare AP, Castellino FJ, Zhong Z, Zlokovic BV. Endothelial protein C receptor-assisted transport of activated protein C across the mouse blood-brain barrier. J Cereb Blood Flow Metab 2009;29(1):25-33.

White TC, Berny MA, Tucker EI, et al. Protein C supports platelet binding and activation under flow: role of glycoprotein 1b and apolipoprotein E receptor 2. J Thromb Haemost 2008;6:995-1002.

Saijoh K, Saito N, Lee MJ, Fujii M, Kobayashi T, Sumino K. Molecular cloning of cDNA encoding a bovine selenoprotein P-like protein containing 12 selenocysteines and a (His-Pro) rich domain insertion, and its regional expression. Mol Brain Res 1995;30:301-311.

Yang X, Hill KE, Maguire MJ, Burk RF. Synthesis and secretion of selenoprotein P By cultured rat astrocytes. Biochim Biophys Acta 2000;1474:390-396.

(56) References Cited

OTHER PUBLICATIONS

Schweizer U, Streckfuss F, Pelt P, et al. Hepatically derived selenoprotein P is a key factor for kidney but not for brain selenium supply. Biochem J 2005;386:221-226.
Hoe HS, Freeman J, Rebeck GW. Apolipoprotein E decreases tau kinases and phospho-tau levels in primary neurons. Mol Neurodegener 2006, 1:18-25.
Hoe HS, Harris DC, Rebeck GW. Multiple pathways of apolipoprotein E signaling in primary neurons. J Neurochem 2005;93:145-155.
Kotilinek, L. A., M. A. Westerman, Q. Wang, K. Panizzon, G. P. Lim, A. Simonyi, S. Lesne, A. Falinska, L. H. Younkin, S. G. Younkin, M. Rowan, J. Cleary, R. A. Wallis, G. Y. Sun, G. Cole, S. Frautschy, R. Anwyl, and K. H. Ashe. 2008. Cyclooxygenase-2 inhibition improves amyloid-beta-mediated suppression of memory and synaptic plasticity. Brain 131:651-664.
Madhusudan, A., C. Sidler, and I. Knuesel. 2009. Accumulation of reelin-positive plaques is accompanied by a decline in basal forebrain projection neurons during normal aging. Eur J Neurosci 30:1064-1076.
Miettinen R, Riedel A, Kalesnykas G, et al. Reelin-immunoreactivity in the hippocampal formation of 9-month-old wildtype mouse: effects of APP/PS1 genotype and ovariectomy. J Chem Neuroanat 2005, 30:105-118.
Pang, P. T., and B. Lu. 2004. Regulation of late-phase LTP and long-term memory in normal and aging hippocampus: role of secreted proteins tPA and BDNF. Ageing Res Rev 3:407-430.
Nakamura, Y., M. Yamamoto, and E. Kumamaru. 2001. Significance of the variant and full-length forms of the very low density lipoprotein receptor in brain. Brain Res 922:209-215.
Miyata, T., K. Nakajima, K. Mikoshiba, and M. Ogawa. 1997. Regulation of Purkinje cell alignment by reelin as revealed with CR-50 antibody. J Neurosci 17(10):3599-3609.
Kim, D. H., H. Iijima, K. Goto, J. Sakai, H. Ishii, H. J. Kim, H. Suzuki, H. Kondo, S. Saeki, and T. Yamamoto. 1996. Human apolipoprotein E receptor 2. A novel lipoprotein receptor of the low density lipoprotein receptor family predominantly expressed in brain. J Biol Chem 271(14):8373-8380.
Trommsdorff, M., M. Gotthardt, T. Hiesberger, J. Shelton, W. Stockinger, J. Nimpf, R. E. Hammer, J. A. Richardson, and J. Herz. 1999. Reeler/Disabled-like disruption of neuronal migration in knockout mice lacking the VLDL receptor and ApoE receptor 2. Cell 97:689-701.
Rice, D. S., and T. Curran. 2001. Role of the reelin signaling pathway in central nervous system development. Annu Rev Neurosci 24:1005-1039.
Komuro, H., and P. Rakic. 1998. Distinct modes of neuronal migration in different domains of developing cerebellar cortex. J Neurosci 18(4):1478-1490.
Howell, B. W., R. Hawkes, P. Soriano, and J. A. Cooper. 1997. Neuronal position in the developing brain is regulated by mouse disabled-1. Nature 389:733-737.
Howell, B. W., F. B. Gertler, and J. A. Cooper. 1997. Mouse disabled (mDab1): a Src binding protein implicated in neuronal development. Embo J 16(1):121-132.
Migaud, M., P. Charlesworth, M. Dempster, L. C. Webster, A. M. Watabe, M. Makhinson, Y. He, M. F. Ramsay, R. G. Morris, J. H. Morrison, T. J. O'Dell, and S. G. Grant. 1998. Enhanced long-term potentiation and impaired learning in mice with mutant postsynaptic density-95 protein. Nature 396:433-439.
Phillips, R. G., and J. E. LeDoux. 1992. Differential contribution of amygdala and hippocampus to cued and contextual fear conditioning. Behav Neurosci 106(2):274-285.
Verhey, K. J. D. Meyer, R. Deehan, J. Blenis, B. J. Schnapp, T. A. Rapoport, and B. Margolis. 2001. Cargo of kinesin identified as JIP scaffolding proteins and associated signaling molecules. J Cell Biol 152(5):959-970.
Bowman, A. B., A. Kamal, B. W. Ritchings, A. V. Philp, M. McGrail, J. G. Gindhart, and L. S. Goldstein. 2000. Kinesin-dependent axonal transport is mediated by the sunday driver (SYD) protein. Cell 103:583-594.
Yu, X. M., R. Askalan, G. J. Keil, 2nd, and M. W. Salter. 1997. NMDA channel regulation by channel-associated protein tyrosine kinase Src. Science 275:674-678.
Herz, J., and U. Beffert. 2000. Apolipoprotein E receptors: Linking Brain Development and Alzheimer Disease. Nat. Rev. Neurosci. 1:51-58.
Weeber, E. J., D. D. Savage, R. J. Sutherland, and K. K. Caldwell. 2001. Fear conditioning-induced alterations of phospholipase C-beta1a protein level and enzyme activity in rat hippocampal formation and medial frontal cortex. Neurobiol Learn Mem 76:151-182.
Weeber, E. J., M. Levy, M. J. Sampson, K. Anflous, D. L. Armstrong, S. E. Brown, J. D. Sweatt, and W. J. Craigen. 2002. The role of mitochondrial porins and the permeability transition pore in learning and synaptic plasticity. J Biol Chem 277(21):18891-18897.
Watase, K., E. J. Weeber, B. Xu, B. Antalffy, L. Yuva-Paylor, K. Hashimoto, M. Kano, R. Atkinson, Y. Sun, D. L. Armstrong, J. D. Sweatt, H. T. Orr, R. Paylor, and H. Y. Zoghbi. 2002. A Long CAG Repeat in the Mouse Scat Locus Replicates SCA1 Features and Reveals the Impact of Protein Solubility on Selective Neurodegeneration. Neuron 34:905-919.
Perez, Y., C. A. Chapman, G. Woodhall, R. Robitaille, and J. C. Lacaille. 1999. Differential induction of long-lasting potentiation of inhibitory postsynaptic potentials by theta patterned stimulation versus 100-Hz tetanization in hippocampal pyramidal cells in vitro. Neuroscience 90(3):747-757.
Parmigiani, S., P. Palanza, J. Rogers, and P. F. Ferrari. 1999. Selection, evolution of behavior and animal models in behavioral neuroscience. Neurosci Biobehav Rev 23:957-970.
Kim, J. J., and M. S. Fanselow. 1992. Modality-specific retrograde amnesia of fear. Science 256(5057):675-677.
Jiang, Y. H., D. Armstrong, U. Albrecht, C. M. Atkins, J. L. Noebels, G. Eichele, J. D. Sweatt, and A. L. Beaudet. 1998. Mutation of the Angelman ubiquitin ligase in mice causes increased cytoplasmic p53 and deficits of contextual learning and long-term potentiation. Neuron 21:799-811.
Howell, B. W., T. M. Herrick, J. D. Hildebrand, Y. Zhang, and J. A. Cooper. 2000. Dab1 tyrosine phosphorylation sites relay positional signals during mouse brain development. Curr Biol 10:877-885.
Howell, B. W., T. M. Herrick, and J. A. Cooper. 1999. Reelin-induced tryosine phosphorylation of disabled 1 during neuronal positioning. Genes Dev 13:643-648.
Rice, D. S., M. Sheldon, G. D'Arcangelo, K. Nakajima, D. Goldowitz, and T. Curran. 1998. Disabled-1 acts downstream of Reelin in a signaling pathway that controls laminar organization in the mammalian brain. Development 125:3719-3729.
Coulin, C., A. Drakew, M. Frotscher, and T. Deller. 2001. Stereological estimates of total neuron numbers in the hippocampus of adult reeler mutant mice: Evidence for an increased survival of Cajal-Retzius cells. J Comp Neurol 439:19-31.
Nguyen, P. V., S. N. Duffy, and J. Z. Young. 2000. Differential maintenance and frequency-dependent tuning of LTP at hippocampal synapses of specific strains of inbred mice. J Neurophysiol 84:2484-2493.
Weeber, E. J., C. M. Atkins, J. C. Selcher, A. W. Varga, B. Mirnikjoo, R. Paylor, M. Leitges, and J. D. Sweatt. 2000. A role for the beta isoform of protein kinase C in fear conditioning. J Neurosci 20(16):5906-5914.
Murphy, K. P., R. J. Carter, L. A. Lione, L. Mangiarini, A. Mahal, G. P. Bates, S. B. Dunnett, and A. J. Morton. 2000. Abnormal synaptic plasticity and impaired spatial cognition in mice transgenic for exon 1 of the human Huntington's disease mutation. Journal of Neuroscience 20(13):5115-5123.
Deller, T., A. Drakew, B. Heimrich, E. Forster, A. Tielsch, and M. Frotscher. 1999. The hippocampus of the reeler mutant mouse: fiber segregation in area CA1 depends on the position of the postsynaptic target cells. Exp Neurol 156:254-267.
Hirotsune, S., T. Takahara, N. Sasaki, K. Hirose, A. Yoshiki, T. Ohashi, M. Kusakabe, Y. Murakami, M. Muramatsu, S. Watanabe,

(56) References Cited

OTHER PUBLICATIONS and et al. 1995. The reeler gene encodes a protein with an EGF-like motif expressed by pioneer neurons. Nat Genet 10:77-83.
D'Arcangelo, G., K. Nakajima, T. Miyata, M. Ogawa, K. Mikoshiba, and T. Curran. 1997. Reelin is a secreted glycoprotein recognized by the CR-50 monoclonal antibody. J Neurosci 17(1):23-31.
Nishikawa, S., S. Goto, et al. (1999). "Transient and compartmental expression of the reeler gene product reelin in the developing rat striatum." Brain Res 850(1-2): 244-248.
Cheng T, Liu D, Griffin JH, et al. Activated protein C blocks p53—mediated apoptosis in ischemic human brain endothelium and is neuroprotective. Nat Med 2003;9:338-342.
Han MH, Hwang SI, Roy DB, et al. Proteomic analysis of active multiple sclerosis lesions reveals therapeutic targets. Nature 2008;451:1076-1081.
Bock, H. H., and J. Herz. 2003. Reelin activates SRC family tyrosine kinases in neurons. Curr Biol 13:18-26.
Bozdagi, O., V. Nagy, K. T. Kwei, and G. W. Huntley. 2007. In vivo roles for matrix metalloproteinase-9 in mature hippocampal synaptic physiology and plasticity. J Neurophysiol 98:334-344.
Chin J, Massaro CM, Palop JJ, et al. Reelin depletion in the entorhinal cortex of human amyloid precursor protein transgenic mice and humans with Alzheimer's disease. J Neurosci 2007, 27:2727-2733.
Knuesel, I., M. Nyffeler, C. Mormede, M. Muhia, U. Meyer, S. Pietropaolo, B. K. Yee, C. R. Pryce, F. M. LaFerla, A. Marighetto, and J. Feldon. 2009. Age-related accumulation of Reelin in amyloidlike deposits. Neurobiol Aging 30:697-716.
Niu S, Renfro A, Quattrocchi CC, Sheldon M, D'Arcangelo G. Reelin promotes hippocampal dendrite development through the VLDLR/ApoER2-Dab1 pathway. Neuron 2004;41:71-84.
Isosaka, T., K. Hattori, et al. (2006). "NMDA—receptor proteins are upregulated in the hippocampus of postnatal heterozygous reeler mice." Brain Res 1073-1074: 11-19.
Valentine WM, Hill KE, Austin LM, Valentine HL, Goldowitz D, Burk RF. Brainstem axonal degeneration in mice with deletion of selenoprotein p. Toxicol Pathol 2005;33:570-576.
Lau LF, Huganir RL. Differential tyrosine phosphorylation of N-methyl-D-aspartate receptor subunits. J Biol Chem 1995;270:20036-20041.
Ogawa, M., T. Miyata, K. Nakajima, K. Yagyu, M. Seike, K. Ikenaka, H. Yamamoto, and K. Mikoshiba. 1995. The reeler gene-associated antigen on Cajal-Retzius neurons is a crucial molecule for laminar organization of cortical neurons. Neuron 14:899-912.
Petralia RS, Esteban JA, Wang YX, et al. Selective acquisition of AMPA receptors over postnatal development suggests a molecular basis for silent synapses. Nat Neurosci 1999;2(1):31-36.
Wirths O, Multhaup G, Czech C, et al. Reelin in plaques of beta-amyloid precursor protein and presenilin-1 double-transgenic mice. Neurosci Lett 2001;316:145-148.
Wu G, Malinow R, Cline HT. Maturation of a central glutamatergic synapse. Science 1996;274(5289):972-976.
Puzzo D, Privitera L, Leznik E, et al. Picomolar amyloid-beta positively modulates synaptic plasticity and memory in hippocampus. J Neurosci 2008;28(53):14537-14545.
Brewer LD, Thibault O, Staton J, et al. Increased vulnerability of hippocampal neurons with age in culture: temporal association with increases in NMDA receptor current, NR2A subunit expression and recruitment of L-type calcium channels. Brain Res 2007;1151:20-31.
Baki L, Shioi J, Wen P, et al. PS1 activates PI3K thus inhibiting GSK-3 activity and tau overphosphorylation: effects of FAD mutations. EMBO J 2004;23:2586-2596.
Brazhnik ES, Vinogradova OS, Stafekhina VS, Kitchigina VF. Acetylcholine, theta-rhythm and activity of hippocampal neurons in the rabbit—I. Spontaneous activity. Neuroscience 1993;53(4):961-970.
Lovell MA, Xiong S, Lyubartseva G, Markesbery WR. Organoselenium (Sel-Plex) decreases amyloid burden and RNA and DNA oxidative damage in APP/PS1 mice. Free Radic Biol Med 2009;46(11):1527-1533.
Morgan SL, Teyler TJ. Electrical stimuli patterned after the theta-rhythm induce multiple forms of LTP. J Neurophysiol 2001;86:1289-1296.
Winters BD, Forwood SE, Cowell RA, Saksida LM, Bussey TJ. Double dissociation between the effects of peri-postrhinal cortex and hippocampal lesions on tests of object recognition and spatial memory: heterogeneity of function within the temporal lobe. J Neurosci 2004;24(26):5901-5908.
Budson AE, Desikan R, Daffner KR, Schacter DL. Perceptual false recognition in Alzheimer's disease. Neuropsychology 2001;15(2):230-243.
Sheldon M, Rice DS, D'Arcangelo G, et al. Scrambler and yotari disrupt the disabled gene and produce a reeler-like phenotype in mice. Nature 1997;389:730-733.
Hughes SW, Crunelli V. Thalamic mechanisms of EEG alpha rhythms and their pathological implications. Neuroscientist 2005;11(4):357-372.
Hodges JR, Graham KS. Episodic memory: insights from semantic dementia. Philos Trans R Soc Lond B Biol Sci 2001;356:1423-1434.
Budson AE, Daffner KR, Desikan R, Schacter DL. When false recognition is unopposed by true recognition: gist-based memory distortion in Alzheimer's disease. Neuropsychology 2000;14(2):277-287.
Monacelli AM, Cushman LA, Kavcic V, Duffy CJ. Spatial disorientation in Alzheimer's disease: the remembrance of things passed. Neurology 2003;61:1491-1497.
Stoppini L, Buchs PA, Muller D. A simple method for organotypic cultures of nervous tissue. J Neurosci Methods 1991;37:173-182.
Mahley, R. W., and S. C. Rall. 1995. Type III Hyperlipoproteinemia (Dysbetalipoproteinemia): The Role of Apolipoprotein E in Normal and Abnormal Lipoprotein Metabolism. In Metabolic and Molecular Bases of Inherited Disease, vol. 61. D. Valle, ed. McGraw-Hill Book Co., New York, p. 1953.
Costa, E., D. R. Grayson, et al. "GABAergic cortical neuron chromatin as a putative target to treat schizophrenia vulnerability." Crit Rev Neurobiol 2003;15(2): 121-42.
Miyata, T., K. Nakajima, et al. "Distribution of a reeler gene-related antigen in the developing cerebellum: an immunohistochemical study with an allogeneic antibody CR-50 on normal and reeler mice." J Comp Neurol 1996; 372 (2): 215-28.
Wang YT, Salter MW. Regulation of NMDA receptors by tyrosine kinases and phosphatases. Nature 1994;369:233-235.
Sheng M, Cummings J, Roldan LA, Jan YN, Jan LY. Changing subunit composition of heteromeric NMDA receptors during development of rat cortex. Nature 1994;368:144-147.
Monyer H, Bumashev N, Laurie DJ, Sakmann B, Seeburg PH. Developmental and regional expression in the rat brain and functional properties of four NMDA receptors. Neuron 1994;12:529-540.
Carmignoto G, Vicini S. Activity-dependent decrease in NMDA receptor responses during development of the visual cortex. Science 1992;258:1007-1011.
Bernard GR, Ely EW, Wright TJ, et al. Safety and dose relationship of recombinant human activated protein C for coagulopathy in severe sepsis. Crit Care Med 2001;29(11)2051-2059.
Costa, E., J. M. Davis, et al. "A GABAergic cortical deficit dominates schizophrenia pathophysiology." Crit Rev Neurobiol 2004;16(1-2): 1-23.
Boyles, J. K., R. E. Pitas, R. W. Mahley, P. J. Gebicke-Haerter, M. J. Ignatius, and E. M. Shooter. 1986. Role for apolipoproteins-E and A-I in nerve degeneration and regeneration. Circulation 74(suppl):II-195.
Cavus, I., P. H. Koo, and T. J. Teyler. Inhibition of long-term potentiation development in rat hippocampal slice by alpha 2-macroglobulin, an acute-phase protein in the brain. J Neurosci Res 1996;43:282-288.
Sweet, H. O., R. T. Bronson, K. R. Johnson, S. A. Cook, and M. T. Davisson. Scrambler, a new neurological mutation of the mouse with abnormalities of neuronal migration. Mamm Genome 1996;7:798-802.
Lambert de Rouvroit, C., and A. M. Goffinet. 1998. The reeler mouse as a model of brain development. Adv Anat Embryol Cell Biol 150:1-106.

(56) References Cited

OTHER PUBLICATIONS

D'Arcangelo, G., G. G. Miao, S. C. Chen, H. D. Soares, J. I. Morgan, and T. Curran. A protein related to extracellular matrix proteins deleted in the mouse mutant reeler. Nature 1995;374:719-723.

Jossin, Yves et al. Processing of Reelin by Embryonic Neurons is Important for Function in Tissue But Not in Dissociated Cultured Neurons. The Journal of Neuroscience, Apr. 18, 2007. 27(16):4243-4252.

Krstic, Dimitrije et al. Regulated Proteolytic Processing of Reelin through Interplay of Tissue Plasminogen Activator (tPA), ADAMTS-4, ADAMTS-5, and Their Modulcators. PLOS One. www.plosone.org. Oct. 2012, Issue 10, e47793.

Smit-Rigter, Laura A. et al. Lifelong Impact of Variations in Maternal Care on Dendritic Structure and Function of Cortical Layer 2/3 Pyramidal Neurons in Rat Offspring. Apr. 2009, vol. 4, Issue 4, e5167. PLoS One. www.plosone.org.

Huang, Cheng-Chiu et al. Chapter 1: The Reelin Gene and Its Functions in Brain Development, pp. 1-13. S.H. Fatemi (ed.), Reelin Glycoprotein: Structure, Biology and Roles in Health an Disease, 2008.

Patterson & Sang, Angiostatin—converting enzyme activities of human matrilysin (MMP-7) and gelatinase B/type IV collagenase (MMP-9). J Biol Chem. Nov. 14, 1997;272(46):28823-5.

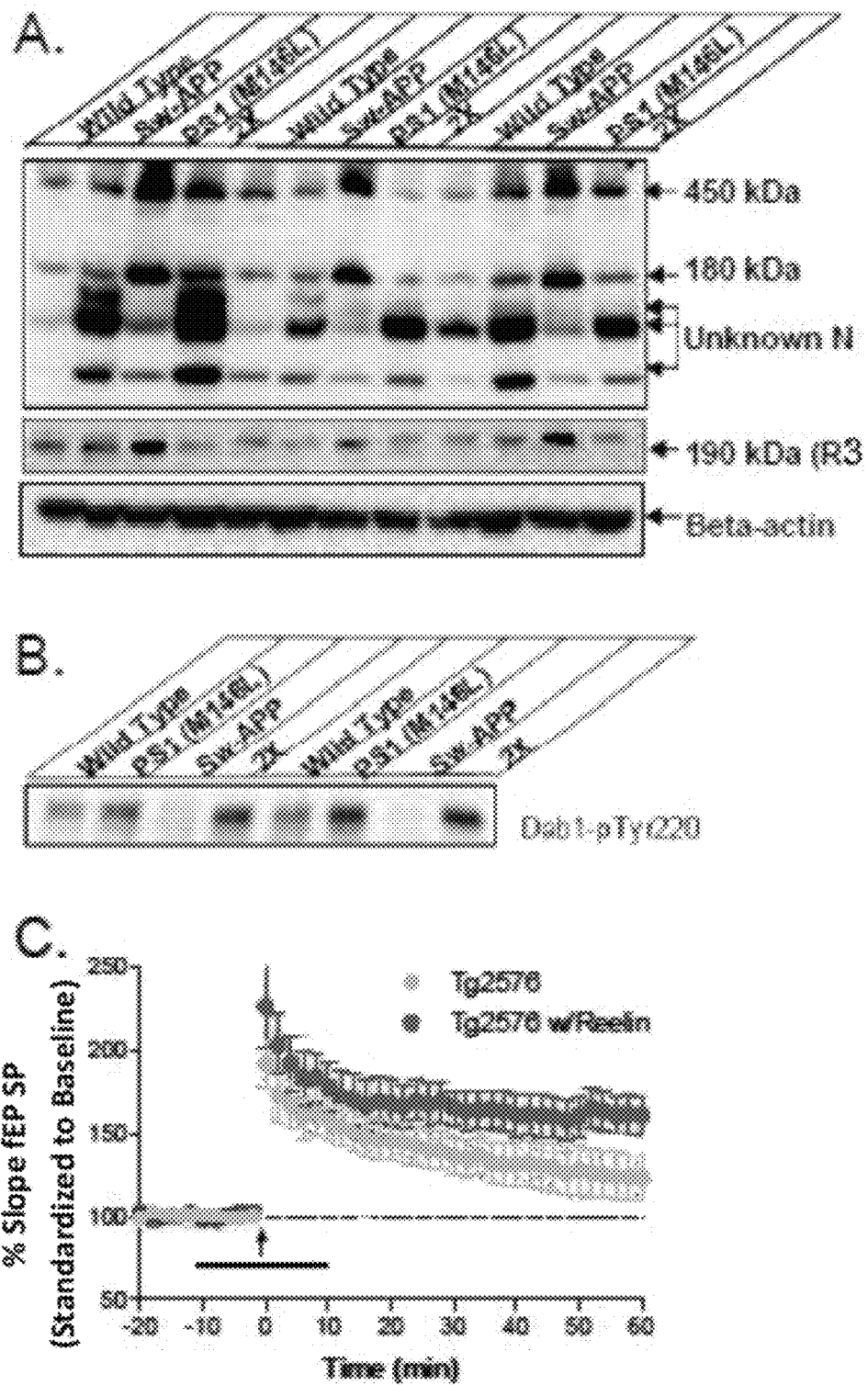
FIGURE 5(A-C)

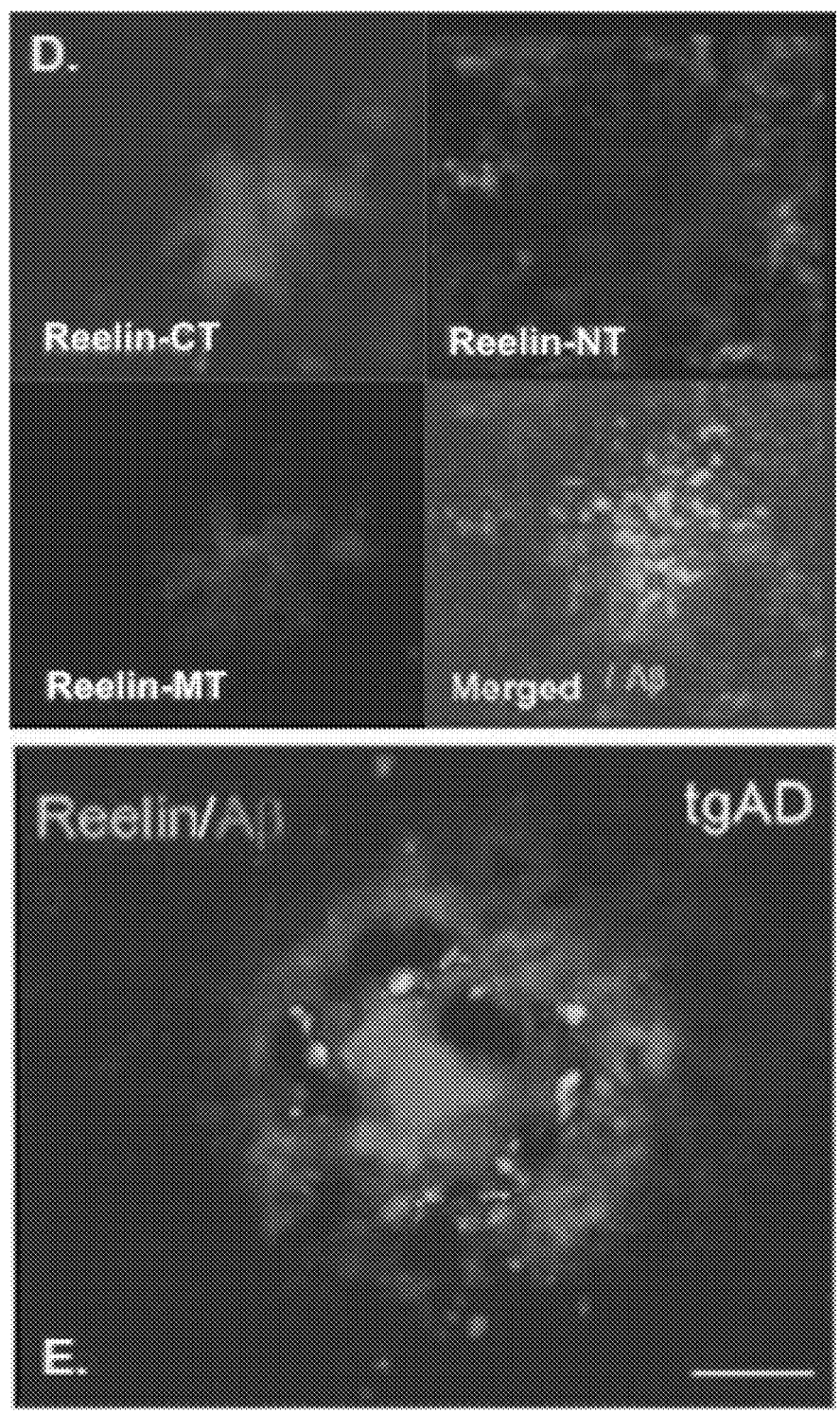
FIGURE 5 (D-E)

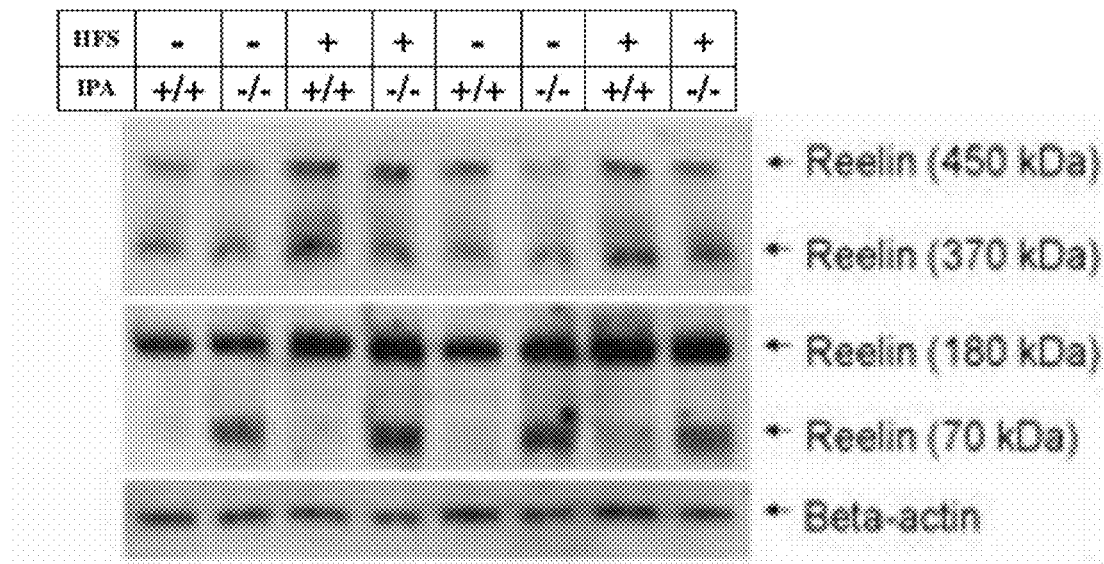
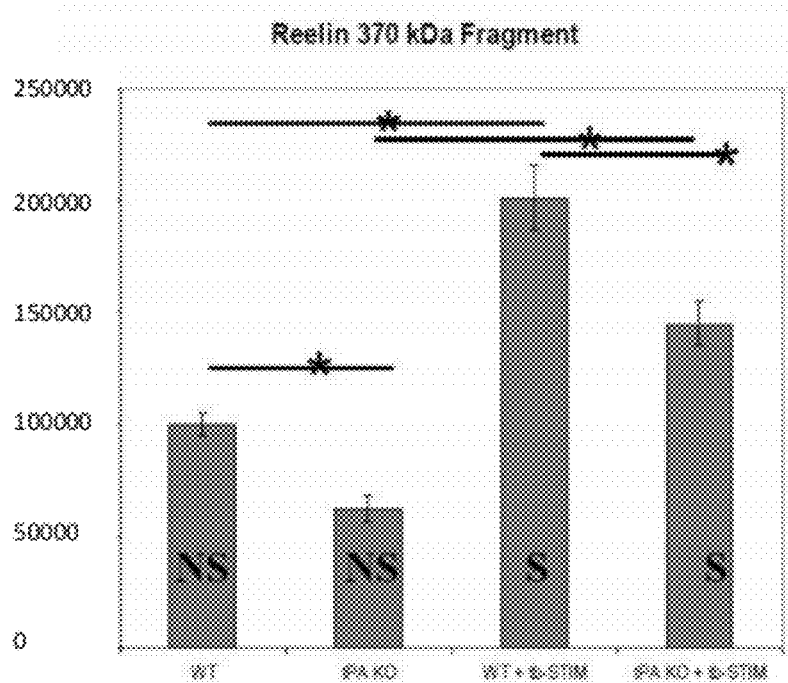
FIGURE 11

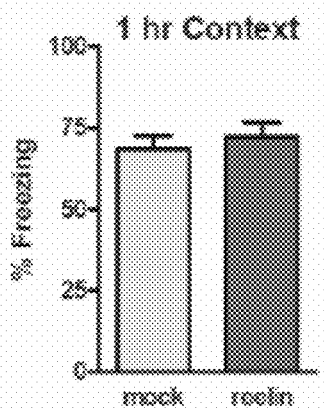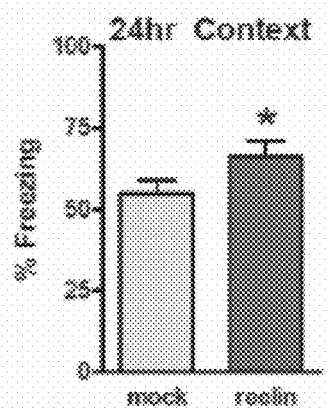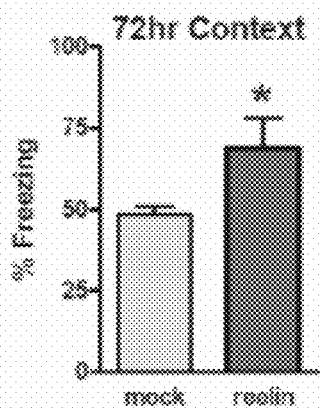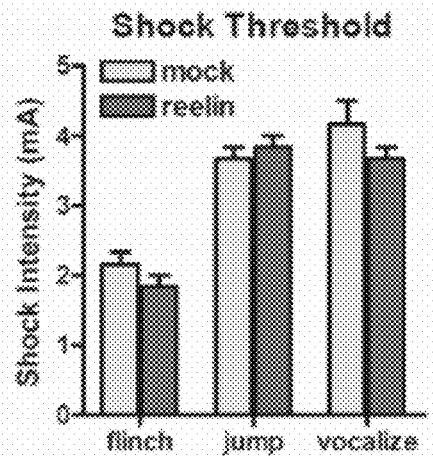

REELIN RESCUES CONGNITIVE FUNCTION

CROSS REFERENCE TO RELATED APPLICATIONS

This application is a continuation of prior filed International Application, Serial Number PCT/US2010/023615 filed Feb. 9, 2010, which claims priority to U.S. Provisional Patent Application No. 61/150,890, filed Feb. 9, 2009; the contents of each of which are herein incorporated by reference.

GOVERNMENT INTEREST STATEMENT

This invention was made with Government support under Grant No. 1R01NS043408-01 awarded by the National Institutes of Health (NIH). The Government has certain rights in the invention.

BACKGROUND OF THE INVENTION

The lipoprotein receptor signaling system is known to play a significant role in the adult CNS such as cholesterol homeostasis, clearance of extracellular proteins, modulating memory formation, synaptic transmission, plasticity and maturation through the activation of numerous signal transduction pathways. Importantly, the lipoprotein receptor ligand apolipoprotein E (apoE) is one of the best validated risk factors for late-onset, sporadic Alzheimer's disease (AD) (Hoe H S, Harris D C, Rebeck G W. Multiple pathways of apolipoprotein E signaling in primary neurons. *J Neurochem* 2005; 93:145-155; Hoe H S, Freeman J, Rebeck G W. Apolipoprotein E decreases tau kinases and phospho-tau levels in primary neurons. *Mol Neurodegener* 2006, 1:18; Hoe H S, Pocivaysek A, Chakraborty G, et al. Apolipoprotein E receptor 2 interactions with the N-methyl-Daspartate receptor. *J Biol Chem* 2006, 281:3425-3431). Moreover, the extracellular matrix protein reelin can bind to both lipoprotein receptors and amyloid precursor protein (APP) and is known to be associated with Aβ plaques in a number of AD mouse models (Chin J, Massaro C M, Palop J J, et al. Reelin depletion in the entorhinal cortex of human amyloid precursor protein transgenic mice and humans with Alzheimer's disease. *J Neurosci* 2007, 27:2727-2733; Hoareau C, Borrell V, Soriano E, Krebs M O, Prochiantz A, Allinquant B. Amyloid precursor protein cytoplasmic domain antagonizes reelin neurite outgrowth inhibition of hippocampal neurons. *Neurobiol Aging* 2008, 29:542-553; Hoe H S, Tran T S, Matsuoka Y, Howell B W, Rebeck G W. DAB1 and Reelin effects on amyloid precursor protein and ApoE receptor 2 trafficking and processing. *J Biol Chem* 2006, 281:35176-35185; and Miettinen R, Riedel A, Kalesnykas G, et al. Reelin-immunoreactivity in the hippocampal formation of 9-month-old wildtype mouse: effects of APP/PS1 genotype and ovariectomy. *J Chem Neuroanat* 2005, 30:105-1180). Aβ accumulation can influence reelin signaling and lipoprotein receptor function, thereby promoting AD pathogenesis and affecting synaptic and cognitive function.

Therefore, what is needed are specific agonists that act upon the lipoprotein receptor system in a manner similar to Reelin for use as therapeutics in the improvement of cognitive function as well as the treatment of neurological disease such as AD and other age-related neurodegenerative disorders.

SUMMARY OF INVENTION

The invention relates generally to methods of influencing, and enhancing, cognitive function by increasing, and/or preventing interference with, Reelin levels as well as the cellular signal transduction initiated or maintained with Reelin or Reelin signaling.

In a first embodiment, the invention includes a method of improving cognitive function, in a subject in need thereof, by administering a therapeutically effective amount of Reelin, a Reelin-specific modulator or an agonist of a lipoprotein receptor to the subject. The lipoprotein receptor can be selected from candidates such as ApoER2 and VLDLR. As disclosed herein, agonists or antagonists of the lipoprotein receptor for use with the inventive method include, but are not limited to, APC, Sep and Fc-RAP. In addition to administering exogenous Reelin, a Reelin-specific modulator, such as a recombinant Reelin fragment, can be used to increase Reelin levels and/or signaling. In an illustrative embodiment, the therapeutically effective amount of Reelin or an agonist of a lipoprotein receptor is approximately 5 nM.

In another embodiment, the invention includes a method of treating a symptom of a disease or disorder of the nervous system by administering a therapeutically effective amount of Reelin, a Reelin-specific modulator or an agonist of a lipoprotein receptor to a subject in need thereof. As with the previous embodiment, the lipoprotein receptor is selected from the group consisting of ApoER2 and VLDLR. The agonists of the lipoprotein receptor for use with the inventive method include, but are not limited to, APC, Sep and Fc-RAP. In this embodiment, the disease or disorder of the nervous system can be selected from the group consisting of fragile X syndrome, William's syndrome, Rett syndrome, Down's syndrome, Angelman syndrome, autism, ischemia, hypoxia, Alzheimer's disease, Reelin deficiency, schizophrenia, neurodegeneration, traumatic brain injury, mental retardation, dementia, and stroke. The therapeutically effective amount of Reelin or an agonist of a lipoprotein receptor is, in one example, approximately 5 nM.

A third embodiment of the invention includes a method of increasing dendritic spine density, in a subject in need thereof, by administering a therapeutically effective amount of Reelin, a Reelin-specific modulator or an agonist of a lipoprotein receptor to the subject. The lipoprotein receptor can be selected from candidates such as ApoER2 and VLDLR. As disclosed herein, agonists of the lipoprotein receptor for use with the inventive method include, but are not limited to, APC, Sep and Fc-RAP. In addition to administering exogenous Reelin, a Reelin-specific modulator, such as a recombinant Reelin fragment, can be used to increase Reelin levels and/or signaling. In an illustrative embodiment, the therapeutically effective amount of Reelin or an agonist of a lipoprotein receptor is about 5 nM.

BRIEF DESCRIPTION OF THE DRAWINGS

For a fuller understanding of the invention, reference should be made to the following detailed description, taken in connection with the accompanying drawings, in which.

n=13; paired t test]. D) No correlation of 1/CV2 ratios and mean EPSCNMDA ratios (after/before reelin) was revealed based on recordings from nine cells (r=0.31; p=0.4; Spearman's test).

Figure 3:
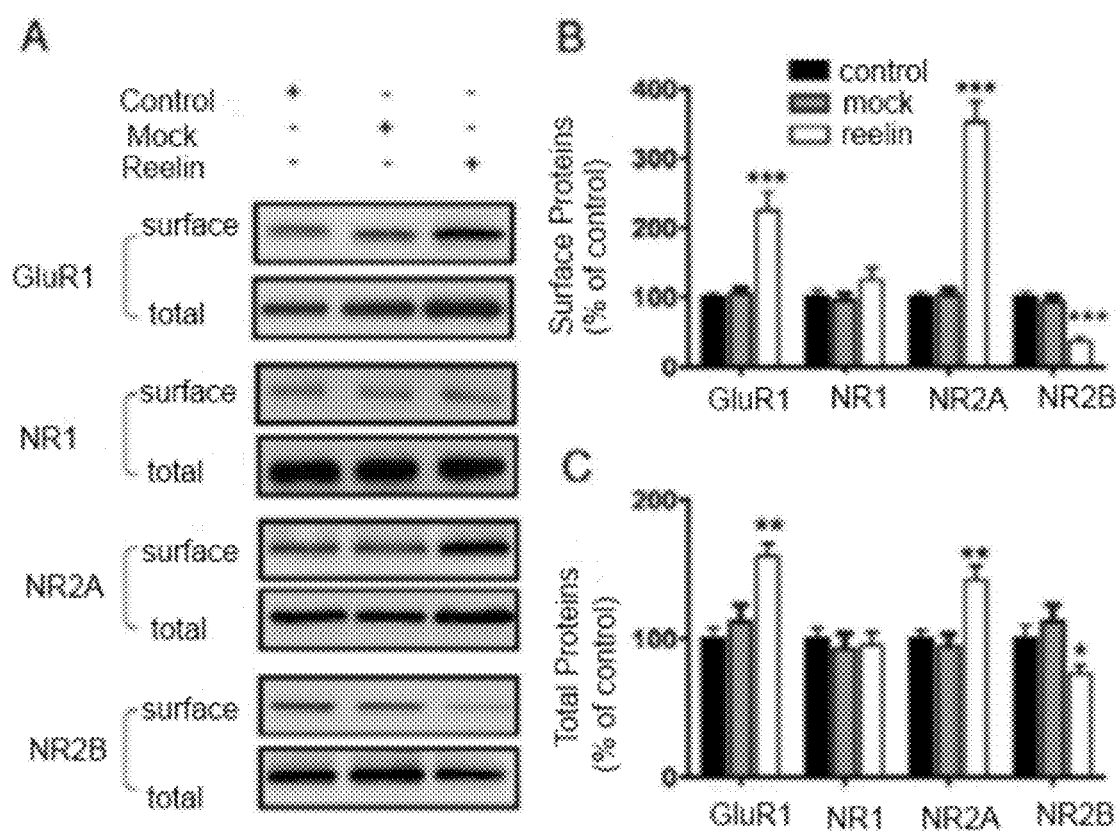

FIG. 3. Reelin signaling alters surface expression and total levels of glutamate receptor subunits. A) Representative blots showing levels of both surface and total GluR1, NR1, NR2A, and NR2B. B) Quantitative results of surface glutamate receptor subunits pooled from 4 experiments. Compared with mock groups, both surface GluR1 and NR2A were significantly increased [GluR1, $F(2,11)=15.56$, *$P<0.001$; NR2A, $F(2,11)=44.9$, *$P<0.001$], and the level of surface NR2B was significantly reduced [$F(2,11)=22.6$, *$P<0.001$] after chronic Reelin treatment. C) Reelin treatment significantly increased levels of total GluR1 [$F(2,11)=11.2$, $P<0.01$], NR2A [$F(2,14)=9.75$, **$P<0.01$], and decreased level of total NR2B [$F(2,11)=4.1$, *$P<0.05$]. In contrast, neither total nor surface (in B) levels of NR1 was observed.

Figure 4:
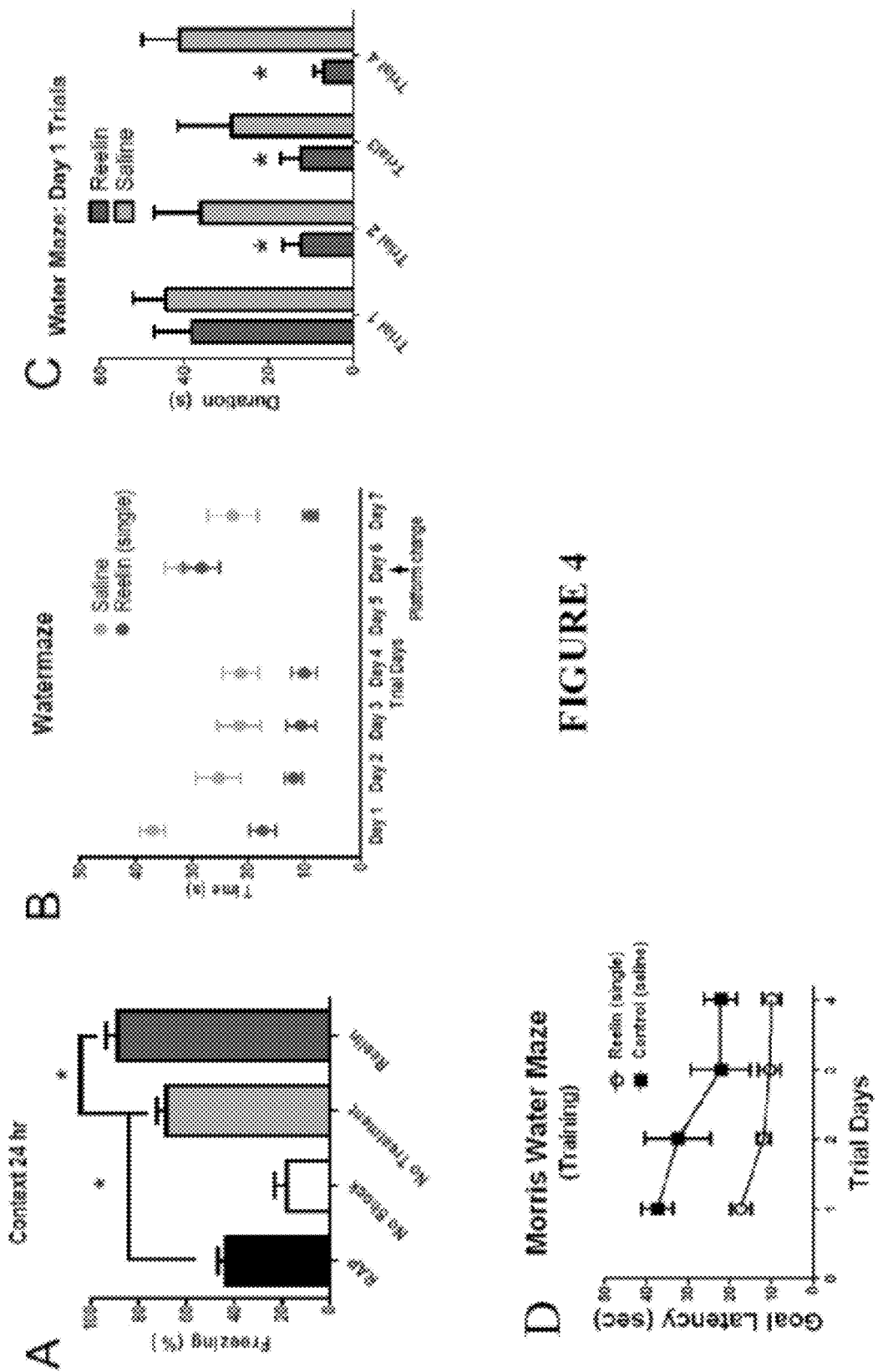

FIG. 4. Reelin supplementation can improve associative learning and spatial learning. A) Wild type mice were given either 5 nM RAP or 5 nM Reelin by bilateral injection into the ventricles 3 hours prior to receiving fear conditioning. 24 hrs after training, mice were placed into the context and freezing measured. RAP was found to inhibit learning and memory while Reelin led to an enhancement (RAP n=9, no shock n=5, no treatment n=7, Reelin n=5; $p>0.05$). B) Wild type mice were trained to find a hidden platform through the Morris Water maze. Mice were given a single injection of either 5 nM Reelin (red circle, n=4) or Vehicle (open circle, n=6). On day 5, a probe trial was given then the mice were trained to find a new platform location on day 6. C) Examination of latencies from individual trials on day 1. (*=$p>0.05$). D) Wild type mice were trained to find a hidden platform through the Morris Water maze. Mice were given a single injection of either 5 nM Reelin (n=4) or Vehicle (n=6).

FIG. 5. Reelin signaling is altered in AD mouse models. A.) Isolated cortices from 14-month old wild type, Tg2576 (Swe-APP), PS1-FAD (M146L), and 2× (SweAPP×M146L) were subjected to western analysis (n=4). No significant differences were detected in Reelin 450, 190 and 180 kDa products in Tg2576 versus wild type, but unidentified N-terminal species recognized by G10 were significantly elevated in Tg2576 and 2× mice. In contrast, Reelin 450 and 180 kDa products were significantly elevated in PS1-FAD and 2× mice ($p<0.05$). B.) There were significant reductions in Dab1-pTyr220 in Tg2576 mice, and significant elevations in both PS1-FAD and 2× mice. C.) Application of Reelin (5 nM) prior to stimulation was able to rescue deficits in HFS-stimulated LTP in area CA1 of Tg2576 mice. D.) The 3-epitope strategy for mapping Reelin processing in vivo was employed on 14-month old Tg2576 horizontal sections. Reelin-CT (G20) and -MT (AF3820) detected Reelin fragments containing R7-8 and R3-6, respectively, sequestered at the core of a dense-core plaque detected with 6E10 (anti-Aβ). E.) Reelin-NT fragments (N-R2) surrounded the plaque core in the tg2576 mouse model. Scale bar=15 μm.

Figure 6:
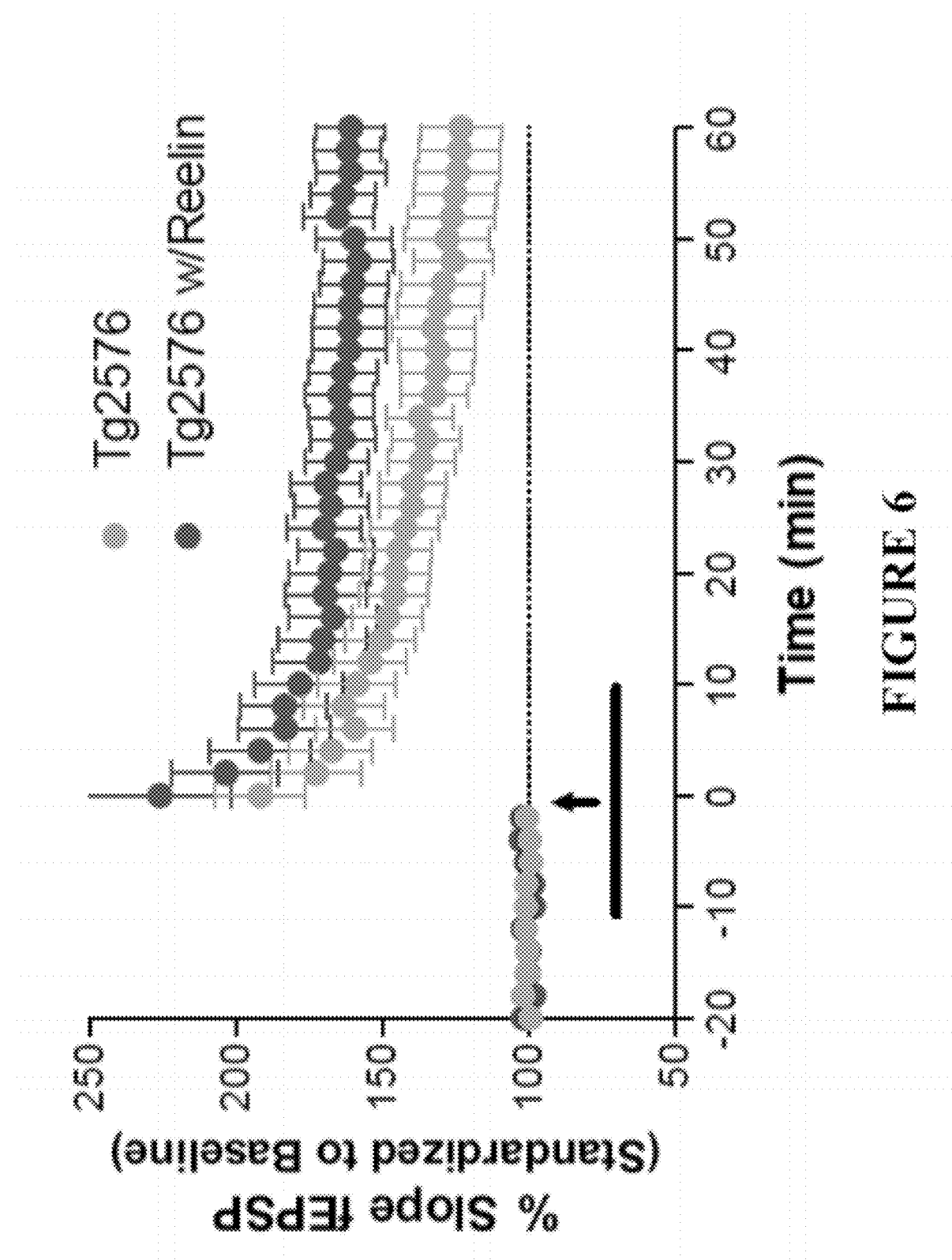

FIG. 6. LTP induction using a standard 2-train, 100 Hz HFS was given to hippocampal slices from 12 month-old Tg2576 mice. A set of slices were perfused with 5 nM reelin. Reelin treated slices showed an increase of LTP induction to that of wild-type levels.

Figure 7:
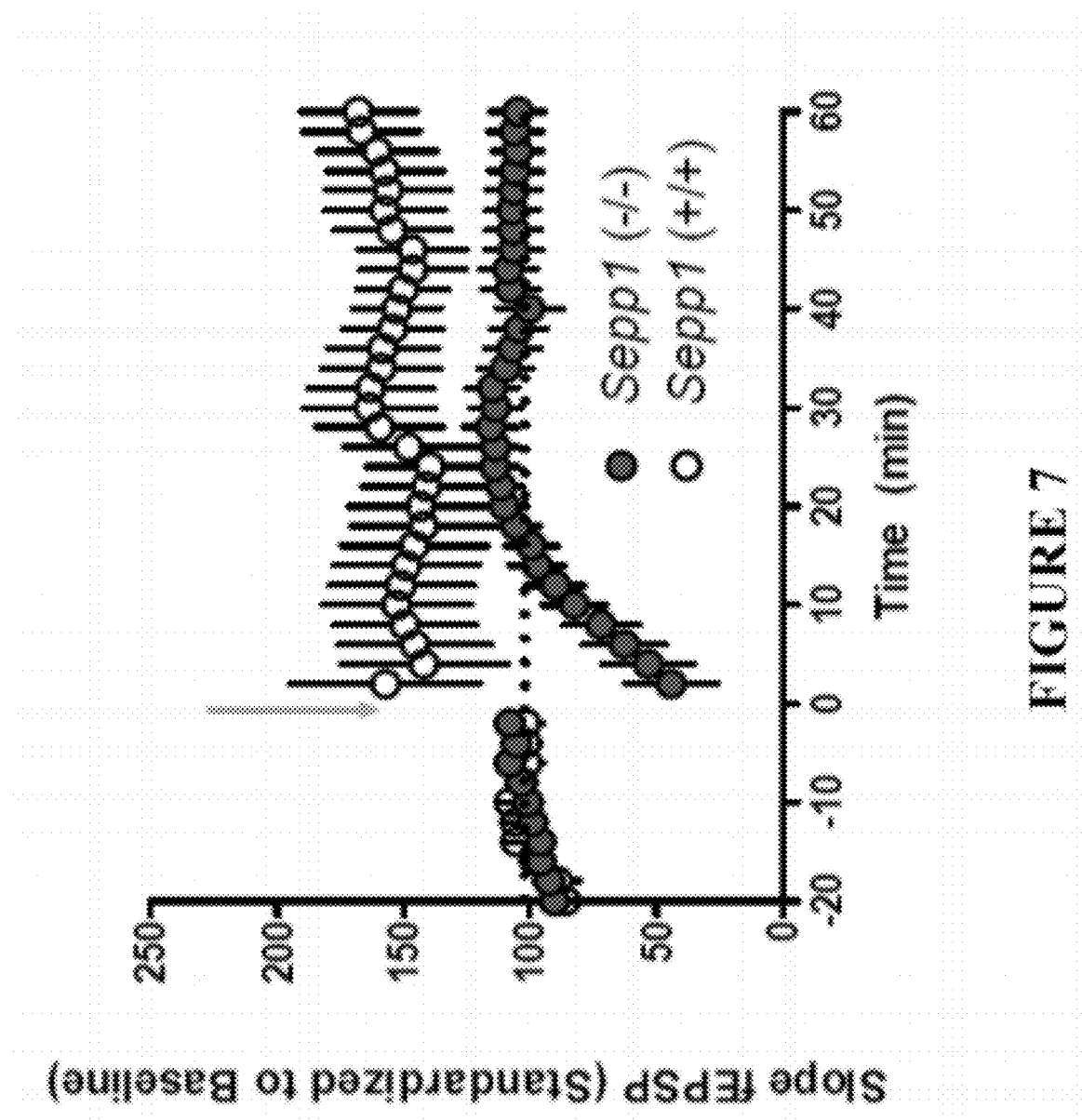

FIG. 7. Targeted deletion of the Selenoprotein P gene results in LTP deficit. Field recordings of acute hippocampal slices show no LTP after 100 Hz stimulation is given (blue arrow) SeP (−/−) n=12, SeP (+/+) n=8. Peters et at 2006

Figure 8:
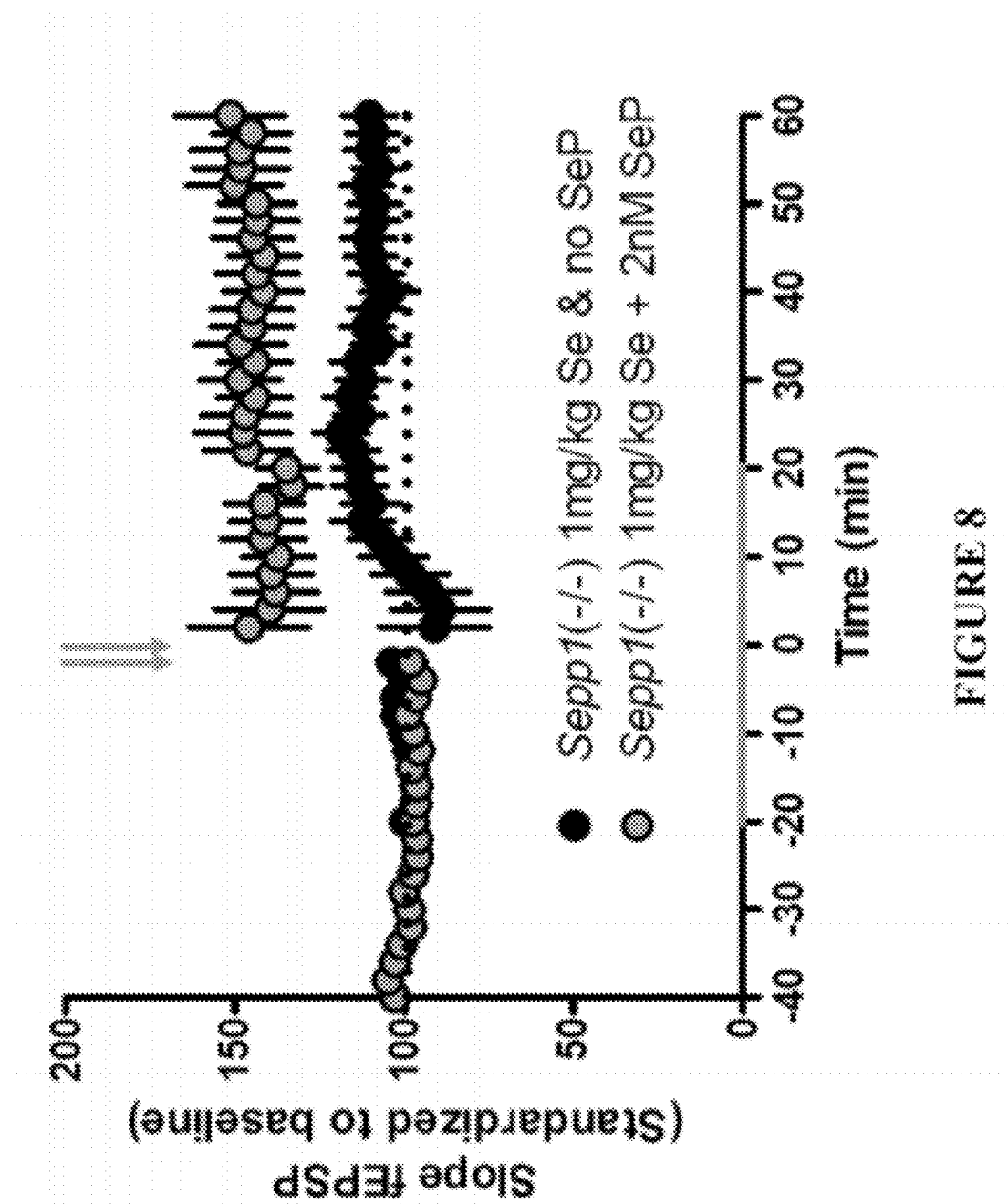

FIG. 8. Addition of Selenoprotein P rescues the LTP deficit in mice lacking the Selenoprotein P gene. Field recordings of acute hippocampal slices in SeP (−/−). Slices treated with 2 nM SeP for 20 min (red line) then given 100 Hz stimulation. SeP (−/−)+2 nM SeP n=16, SeP (−/−) no SeP n=28.

Figure 9:
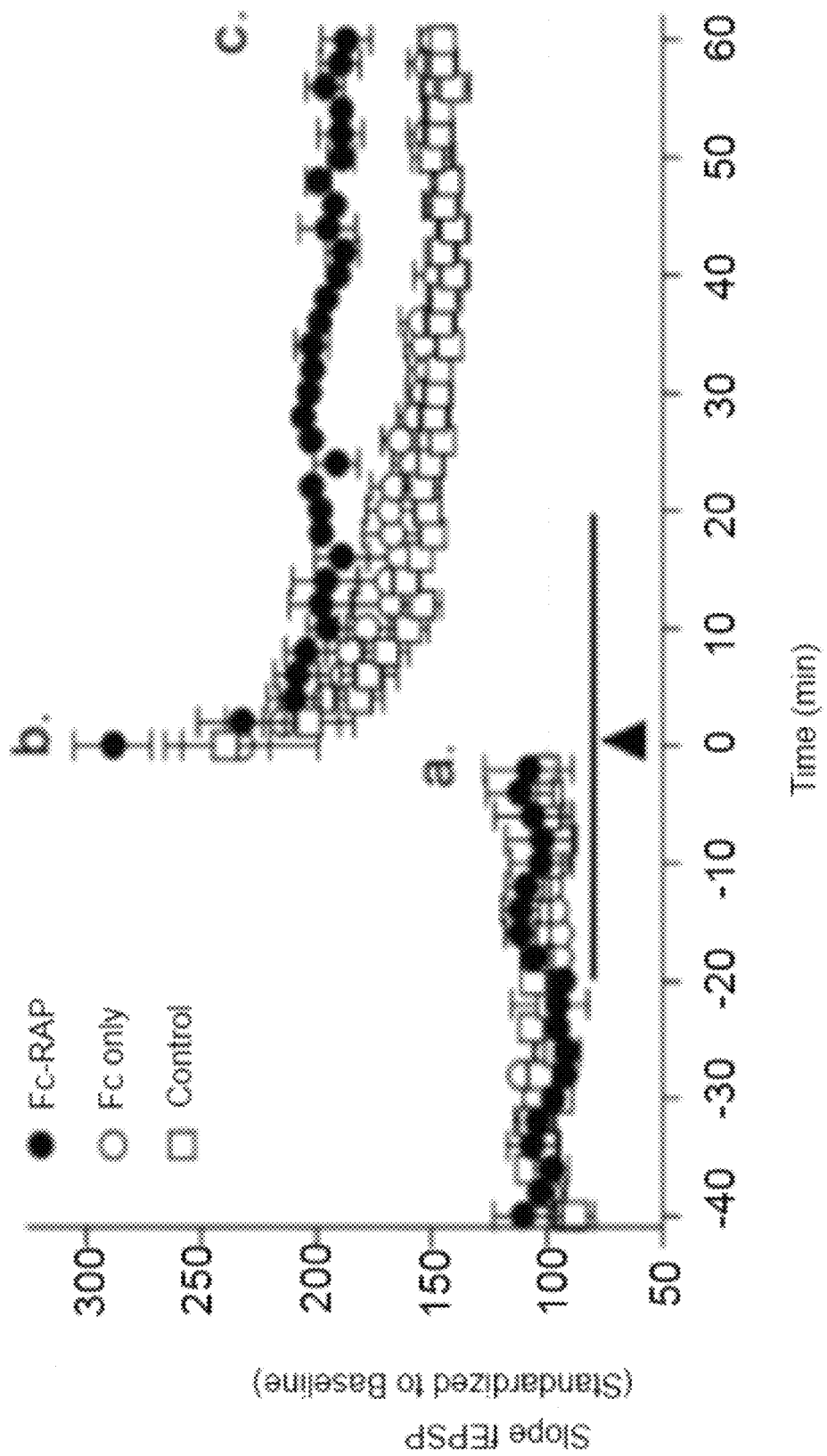

FIG. 9. Perfusion with Fc-RAP enhances hippocampal LTP induction. Hippocampal slices were perfused with Fc-RAP (10 μg/ml), Fc (10 μg/ml), or control medium. Baseline synaptic responses (a) and potentiation immediately following HFS (b) and up to 60 min after HFS (c) were recorded. The arrowhead represents LTP induced with two trains of 1-s-long, 100-Hz stimulation, separated by 20 s. The horizontal line indicates application of Fc-RAP, Fc, or control medium. Results are shown as means±standard errors of the mean. fEPSP, field excitatory postsynaptic potential Strasser et al 2004.

Figure 10:
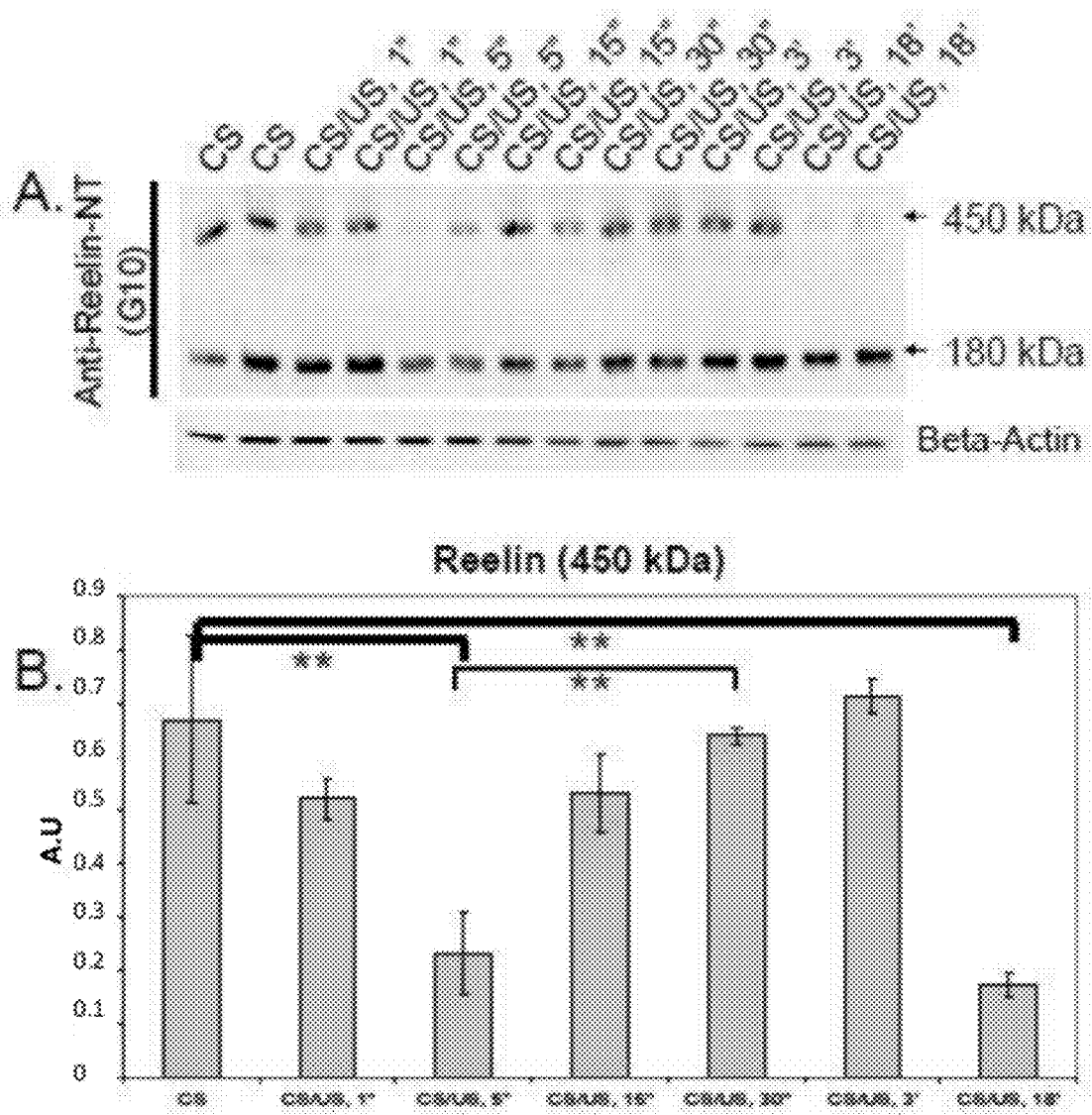

FIG. 10. Contextual fear conditioning alters Reelin levels. Wild type mice were trained with a 3-shock, contextual fear conditioning protocol (CFC). Non-shocked mice (CS) were used as a negative control and shocked, context-exposed mice (CS/US) had their hippocampus removed at 1, 5, 15, 30, and 180 minutes after training, as well as 18 hours post-training (n=4, time point). Reelin was detected in hippocampal homogenates using anti-Reelin (G10) (A) and the levels of full-length Reelin were quantitated (B). The asterisks denote statistical significance following a two-tailed t-test, where $p<0.5$.

FIG. 11. HFS alters Reelin metabolism in a tPA-dependent manner. Acute hippocampal slices were stimulated using TB-STIM (theta burst stimulation) consisting of 5 trains at theta-burst across the Schaffer collateral. Hippocampi were harvested 15 minutes later and homogenates were subjected to western blot analysis and detected with anti-Reelin (G10) (n=3 per group). Non-stimulated is denoted as NS and stimulated as S. The 370 kDa was quantified and statistically analyzed using a two tailed t-test (*, $p<0.05$).

Figure 12A:
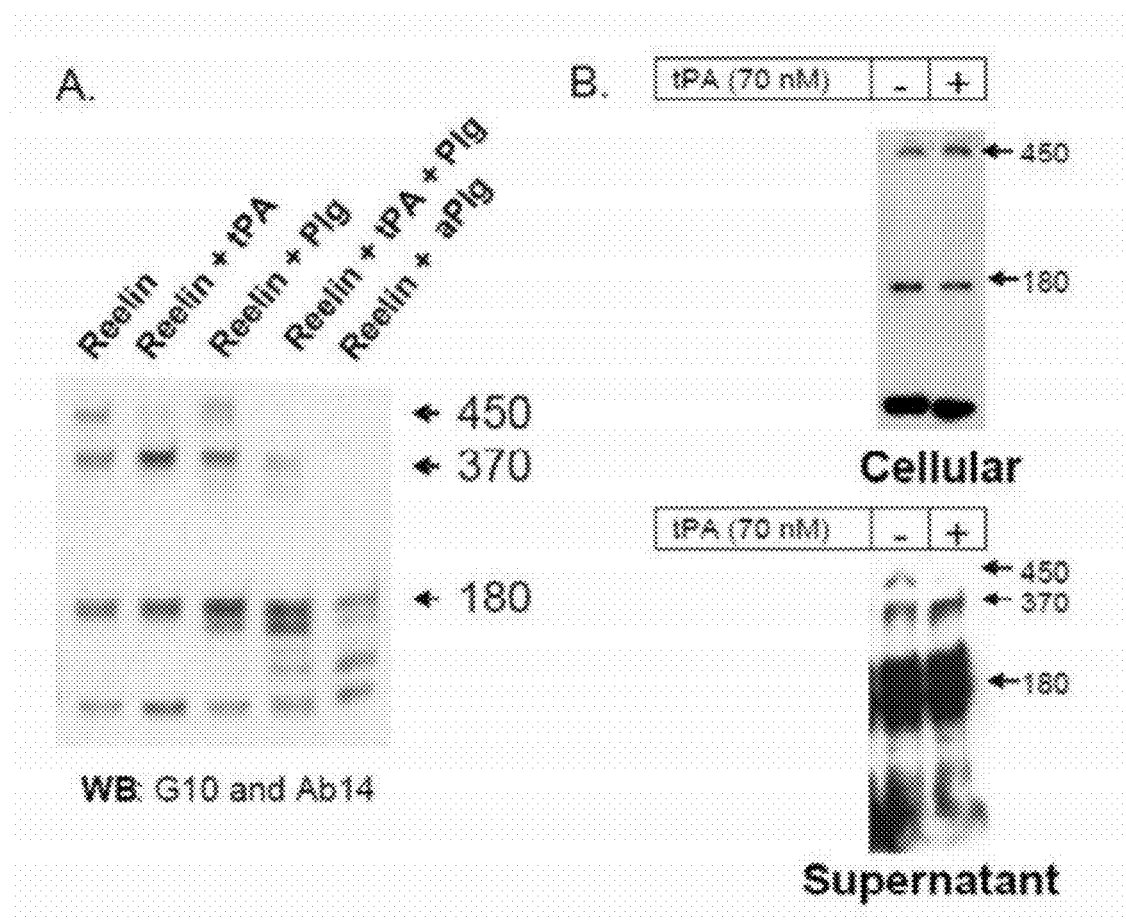

FIG. 12A. tPA modulates Reelin processing. A.) The ability of tPA/plasminogen to affect Reelin processing was determined by reacting Reelin (50 nM) with tPA (60 ug/ml), inactive plasminogen (18 ug/ml), tPA and plasminogen, and Plasmin (active, 0.5 U/ml) in PBS for 45 minutes at 37° C. Reactions were run on Westerns (at 1:10) and probe with anti-Reelin (G10, an N-R2 recognizing antibody) and ant-I Reelin (Ab14, a R7-8 recognizing antibody) B). The ability of tPA to affect Reelin metabolism in primary cortical neurons was determined by incubating cells in fresh supernatant for 24 hours with 70 nM tPA. Both cellular and supernatant protein extracts were subjected to Western analysis and detection with G10.

Figure 12B:
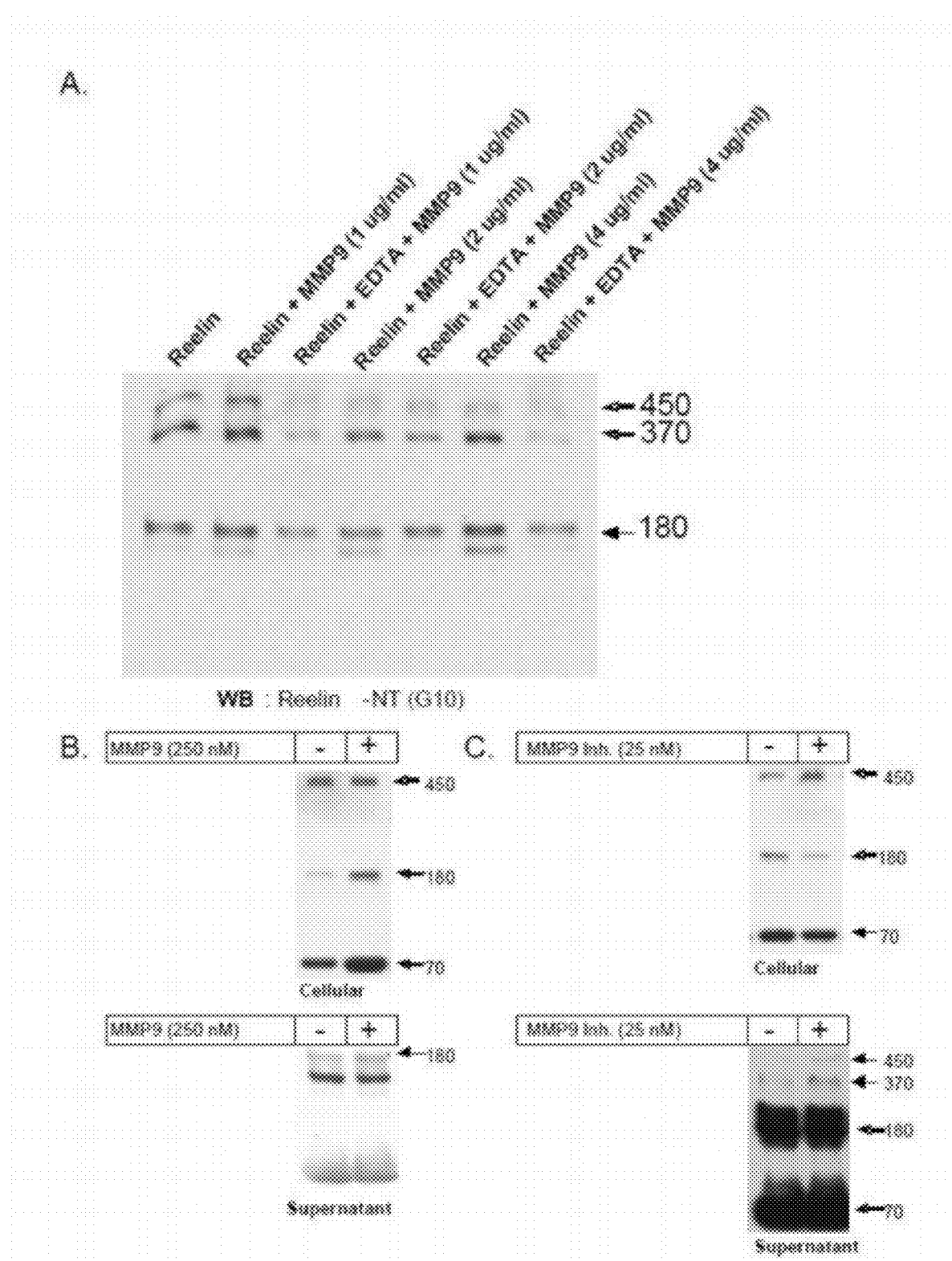

FIG. 12B. MMP-9 modulates Reelin processing. The ability of MMP-9 (active; Calbiochem, PF140) to affect Reelin processing was determined by reacting Reelin (50 nM) with different concentrations of MMP-9 (1-4 ug/ml) in PBS at 37° C. for 3 hours. EDTA (10 mM) was included as a negative control, as it blocks MMP9 activity. Western blots were run on 1:10 of the reaction and probed with anti-Reelin (G10) (B). The ability of MMP-9 (250 nM) and the MMP-9 inhibitor (25 nM; Calbiochem 444278) to affect Reelin processing in primary cortical neurons was determined after 24 hours in both cellular and supernatant extracted proteins.

Figure 13:
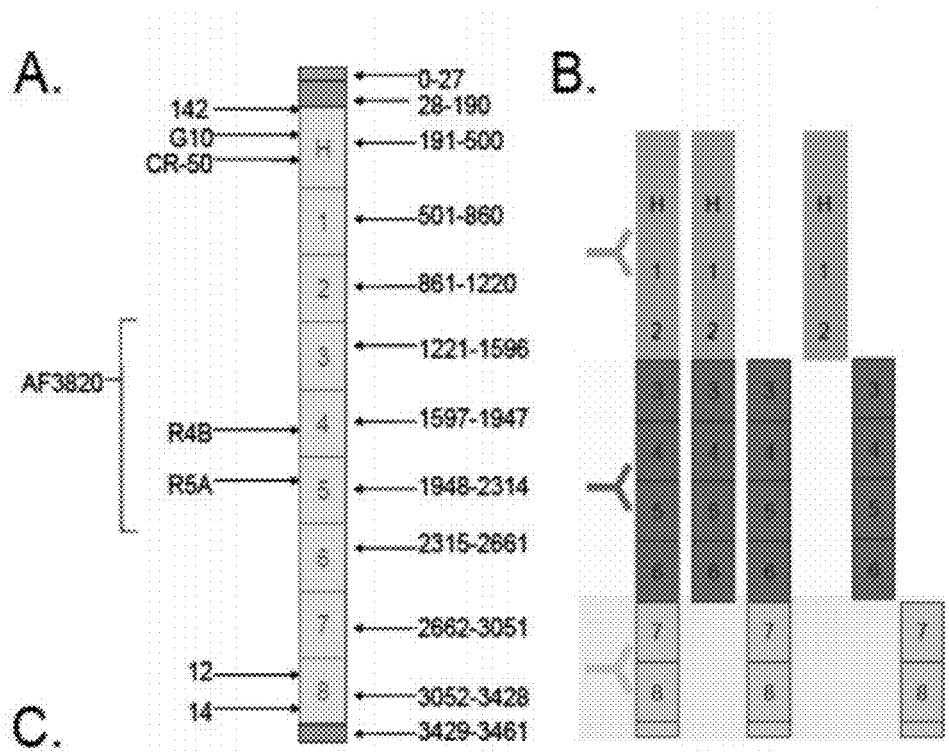

FIG. 13. Tri-epitope mapping. (A). Reelin consists of an N-terminal region followed by the CR-50 electrostatic domain (purple), an F-spondin domain (H), and 8 consecutive EGF-like repeats. (B). Antibodies that distinctly recognize the N-R2, R3-R6, and R7-R8 regions of Reelin can be used to determine the distribution of full-length Reelin and its major fragments. (C). Antibodies that will be employed in the 3-epitope approach are listed.

Figure 14:
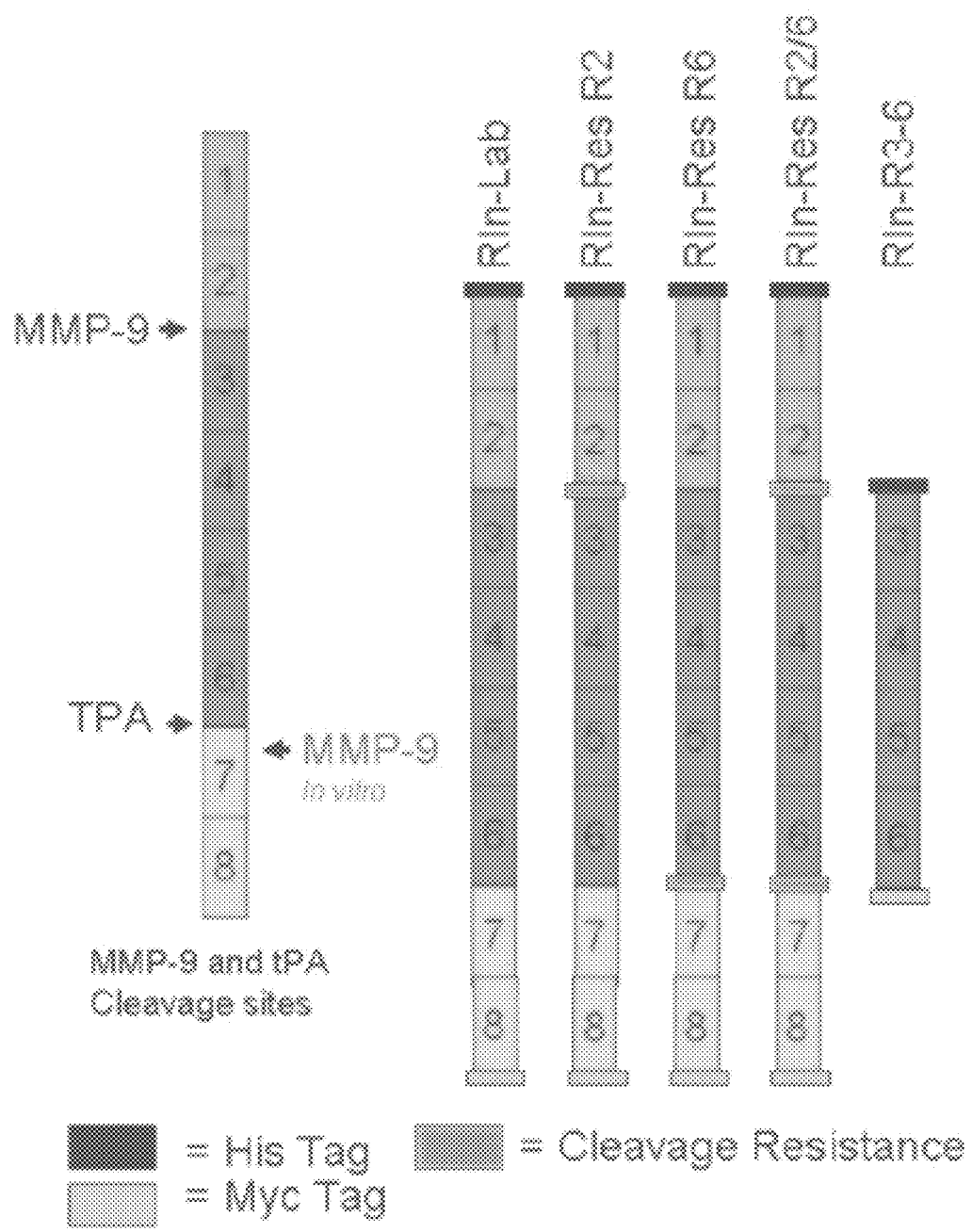

FIG. 14. Illustration of constructs to be used in SA2 and SA3 and sites of Reelin cleavage. MMP-9 can cleave between regions 2 and 3, but has also been shown to cleave in region 7 during in vitro reactions only. tPA can cleave between regions 6 and 7. Proposed constructs are made without the in vitro MMP-9 binding site a with both C and N terminal tags. Rln-Res=Reelin Cleavage Resistant; Rln-Lab=Reelin labile.

Figure 15:
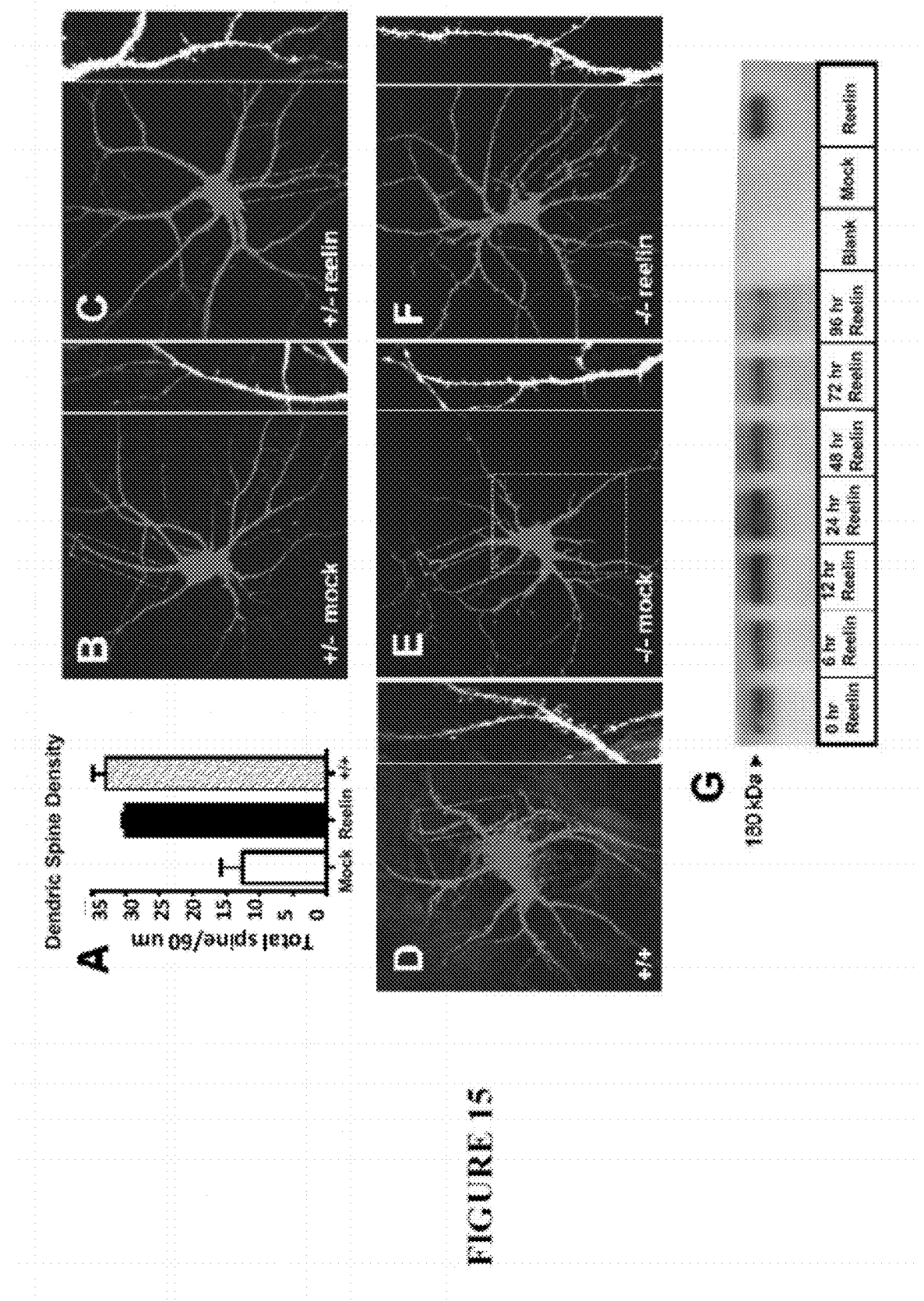

FIG. 15. Reelin effects on dendritic spine density. Reelin was applied chronically to primary hippocampal neuronal cultures to examine its effect on dendritic spine density. (A) Dendritic spines on a WT neuron are shown in an enlarged photo of a representative primary dendrite. (B and C) Dendritic spines are reduced in the HRM compared to WT mice but after treatment with reelin, spine density is rescued. (D and E) Dendritic spines are very sparse in the knockout reelin mice but after treatment with reelin, spine density deficits are rescued. (F) Dendritic spines were quantified using a confocal microscope. Dendritic spines were defined as any protrusion from a primary dendrite excluding any secondary dendrites. Dendritic spines were counted and measured every 50 um of the dendrite. There is a significant increase in spines in reelin-treated cells (n=3) versus mock-treated cells (n=3). (G) Reelin levels in culture were determined by a Western Blot. Samples were taken out of culture at 0, 6, 12, 24, 48, 72, and 96 hrs to determine the levels of reelin degradation in vitro. The last column of reelin represents the native in the concentration administered to the culture. Reelin was present up until 96 hours after introduction to culture and degradation did not begin until 72 hours.

Figure 16:
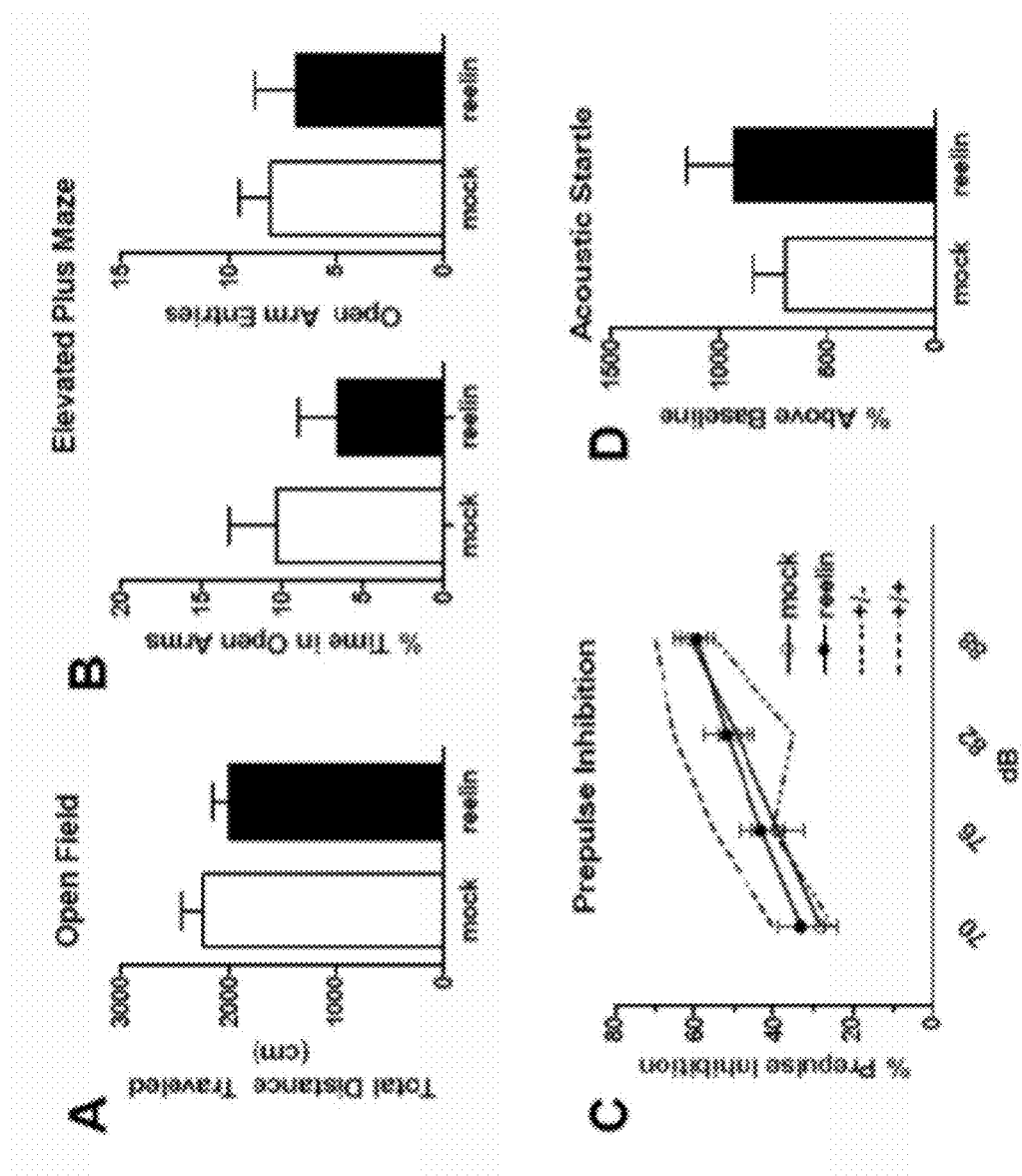

FIG. 16. Locomotor activity, nociception and anxiety are unaltered by drug treatments. (A) Open field behavior utilized to evaluate locomotor activity. The total distance traveled during the 15 min test was similar for the three conditions (mock HRM n=13, reelin HRM n=13, Rap WT n=10; ANOVA p=0.23). (B) Elevated Plus Maze utilized to determine anxiety. Both the percent of time spent in the open arms and the number of open arm entries were similar for the three conditions (mock HRM n=11, reelin HRM n=10, Rap WT n=13; percent time ANOVA p=0.49 and open arm entries ANOVA p=0.63). (C) Prepulse inhibition (D) Acoustic startle utilized to evaluate startle response. The startle response to a 120 dB acoustic stimulation is similar for the three conditions (mock HRM n=14, reelin HRM n=16, Rap WT n=15; ANOVA p=0.56). Results from Qiu et al. (2005) are depicted with dashed lines for reference.

FIG. 17. HRM contextual fear conditioning deficits are rescued by application of exogenous reelin. (A) Freezing during the conditioning paradigm was similar for both conditions (mock HRM n=16, reelin HRM n=16). The tone is represented by the black bar and the shock by the black arrows. Freezing during reintroduction to the conditioning context. (B) Freezing was similar for the three conditions 1 hr post conditioning (mock HRM n=13, reelin HRM n=13). (C) Reelin-treated HRM freezing was significantly greater than mock-treated HRM 24 hrs post conditioning (mock HRM n=16, reelin HRM n=16; t-test p=0.02) and (D) 72 hrs post conditioning (mock HRM n=5, reelin HRM n=4; t-test p=0.026). (E) Shock threshold analysis to evaluate nociception. The shock intensity in which mice flinched, jumped, or vocalized was similar for both conditions (mock HRM n=3, reelin HRM n=3; ANOVA p=0.22).

Figure 18:
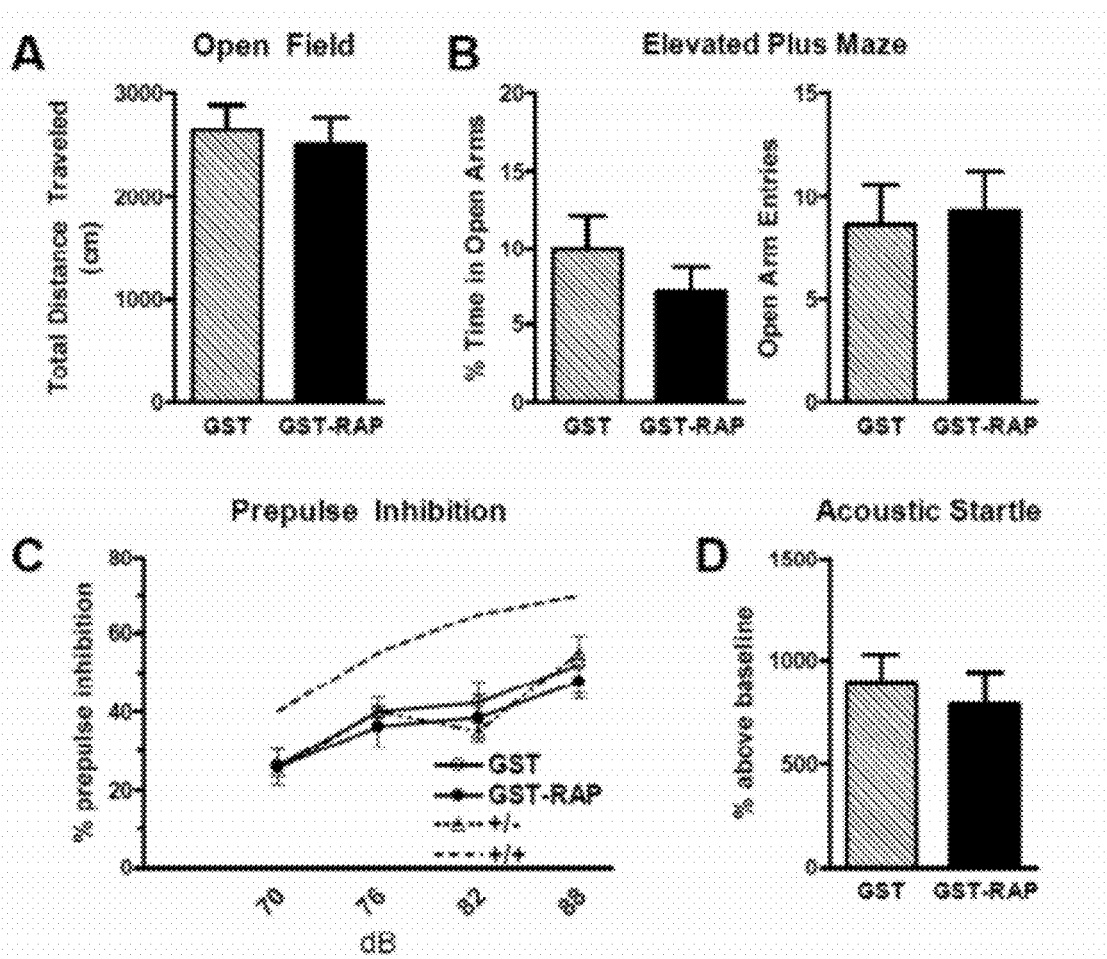

FIG. 18. Locomotor activity, nociception and anxiety are unaltered by drug treatments. (A) Open field behavior utilized to evaluate locomotor activity. The total distance traveled during the 15 min test was similar for the two conditions (Rap WT n=10). (B) Elevated Plus Maze utilized to determine anxiety. Both the percent of time spent in the open arms and the number of open arm entries were similar for both conditions (Rap WT n=13; percent time ANOVA p=0.49 and open arm entries ANOVA p=0.63). (C) Prepulse inhibition, Results from Qiu et al. (2005) are depicted with dashed lines for reference. (D) Acoustic startle utilized to evaluate startle response. The startle response to a 120 dB acoustic stimulation is similar for both conditions (Rap WT n=15; ANOVA p=0.56).

FIG. 19. (A) Freezing during the conditioning paradigm was similar for both conditions (Rap WT n=13). The tone is represented by the black bar and the shock by the black arrows. Freezing during reintroduction to the conditioning context. (B) Freezing was similar for both conditions 1 hr post conditioning (Rap WT n=9). (C) RAP-treated WT freezing was significantly less than vehicle-treated WT (Rap WT n=13) 24 hrs post conditioning and (D) 72 hrs post (Rap WT n=6). There was no difference between mock-treated HRM freezing and Rap-treated WT freezing at any time tested (See FIGS. 17B-C) (E) Shock threshold analysis to evaluate nociception. The shock intensity in which mice flinched, jumped, or vocalized was similar for both conditions (Rap WT n=4; ANOVA p=0.22).

DETAILED DESCRIPTION OF THE PREFERRED EMBODIMENT

Recent research has established a role for lipoprotein receptors in cognitive processes and implicated this receptor family in the pathological processes that underlie the progression of AD. Two of the major ligands for these receptors, apoE and reelin, appear to have signaling capabilities that can significantly impact synaptic function, directly interact with APP and modulate its metabolism, and are sensitive to $A\beta$ accumulation. $A\beta$ accumulation disrupts lipoprotein receptor signaling, resulting in concomitant disruption of cognitive function. Furthermore, interference of reelin and/or lipoprotein receptor signaling results in aberrant APP metabolism and $A\beta$ clearance that in turn exacerbates $A\beta$ accumulation and plaque deposition. Therefore, increased reelin signaling through direct reelin application or usage of other lipoprotein receptor agonists can be used to mitigate $A\beta$-dependent cognitive disruption and progression of plaque pathology.

Reelin: In the adult hippocampus, the glycoprotein Reelin is expressed by interneurons residing primarily in the hilar region of dentate gyms, and the stratum lacunosum-moleculare layer of the hippocampus proper. Reelin-expressing cells can also be found in stratum oriens and stratum radiatum of area CA1 and CA3 and is associated with pyramidal cells of the hippocampus. Induction of long-term potentiation (LTP), a form of synaptic plasticity that results in a lasting increase in synaptic efficacy, requires NMDAR (NMDARs) activation and the subsequent up-regulation of AMPA receptor expression and function. Changes in AMPA receptors (AMPARs) can be achieved either by increased subunit phosphorylation or by increased subunit synthesis and trafficking to the specific synaptic sites. In contrast, NMDARs serve as coincidence detectors and play a major role in the induction of synaptic plasticity. The opening of NMDAR ion channels requires both glutamate binding and post-synaptic membrane depolarization. Some NMDAR subunits, such as NR1, NR2A and NR2B are also subjected to modulatory phosphorylation at serine/threonine or tyrosine residues. Phosphorylation of NMDAR subunits modulates both channel kinetics and trafficking to synaptic sites. It follows that if reelin were important for modulation of synaptic plasticity, then NMDARs and AMPARs would be logical targets given their importance in induction and expression of synaptic plasticity.

APC: Activated protein C (APC) is a serine protease that possesses both anticoagulant and cytoprotective properties that are currently being exploited for the treatment of conditions such as sepsis, stroke and multiple sclerosis. The anticoagulant properties of APC are achieved through the protein C (PC) pathway, while its cryoprotective effects are orchestrated through PAR1 (protease activated receptor; and PAR3, endothelial PC receptor (EPCR) and ApoER2. In mice, APC has been found to protect against diabetic endothelial and glomerular injury, multiple sclerosis and ischemia/reperfusion injury in the kidney and lung.

APC has already been approved by the U.S. Food and Drug Administration for use in adult severe sepsis and is currently in Phase I/IIa clinical trials for the treatment of ischemic stroke (National Institutes of Health, Activated Protein C in Acute Stroke Trial (APCAST), 2010). Numerous groups have also recently developed APC variants that possess less anticoagulant activity, which has proven to limit APC's clinical efficacy. Specifically, a mutant designated 3K3A-APC has 80% reduced anticoagulant activity but retains normal PAR1 and EPCR-dependent anti-apoptotic activity. Relevant to the use of APC to treat neuropathologies, APC and APC variants have been found to effectively cross the BBB via EPC-mediated transport.

Recently, APC has been found to activate the Reelin signaling cascade via high affinity ligation to ApoER2. Specifically, APC-treated monocytes demonstrated increased active Dab1 (Tyr220-p), Akt Ser473-p, and GSK3beta Ser9-p levels. Pre-treatment with RAP or knocking down of ApoER2 were found to attenuate these effects, while inhibitors of EPCR and PAR1 had no effect. Interestingly, APC was found to bind to ApoER2 with 30 nM affinity, but not to soluble VLDLR. To relate APC's effects to ApoER2 signaling, RAP was found to block APC-mediated inhibition of endotoxin-induced tissue factor pro-coagulant activity of U937 cells.

Recent work has highlighted the importance of Reelin signaling in normal learning and memory (Weeber E J, Beffert U, Jones C, et al. Reelin and ApoE receptors cooperate to enhance hippocampal synaptic plasticity and learning. *J Biol Chem* 2002, 277:39944-39952), as well as pathological instances where this signaling is perturbed. APC is now a candidate modulator of Reelin signaling, as it appears to have the structural moieties to bind to ApoER2 and activate downstream effectors. It is of immense scientific and clinical relevance that APC modulation of Reelin signaling be tested, as it could yield novel therapeutic avenues.

SePP1: Approximately 60% of selenium in plasma is present in selenoprotein P. This protein differs from other selenoproteins in that it incorporates up to 10 Se atoms per molecule in the form of selenocysteine as opposed to single selenocysteines. Selenoprotein P is abundant throughout the body, suggesting that one function is to serve as a primary transporter in systemic selenium delivery. This is especially evident in the CNS where selenoprotein P levels can be maintained independent of plasma selenium. However, genetic ablation of selenoprotein P results in reduced, but not a commensurate decrease in CNS-associated selenium levels, suggesting that other selenium proteins compensate for the selenoprotein P deficiency and supporting the hypothesis that basal selenium levels are essential for the brain and have a priority for systemically available selenium. Sepp1 (−/−) mice fed a selenium-deficient diet show severe motor dysfunction associated and associated neuronal degeneration, which can be prevented by supplementation with high dietary selenium.

Reduced dietary selenium can have significant effects on levels of selenoproteins involved in oxidative stress and their related effects on glutathione peroxidases, thioredoxin reductases and methionine sulfoxide reductases. Selenium, through incorporation into selenoproteins, provides protection from reactive oxygen species (ROS)-induced cell damage. This is interesting in light of the role of oxidative stress and subsequent production of ROS in neurodegenerative disorders such as Alzheimer's disease, Parkinson's disease and Duchenne muscular dystrophy. The inventors have previously examined the consequences of selenoprotein P deficiency on cognitive capacity and synaptic function with a focus on the hippocampus, an area of the CNS intimately involved in learning and memory processes. Sepp1 (−/−) mice demonstrated no overt behavioral phenotype, but were found to have a subtle disruption in acquisition of spatial learning and memory. In contrast, synaptic transmission was altered and short- and long-term synaptic plasticity was severely disrupted in area CA1 of hippocampus. Interestingly, the inventors found that when Sepp1 (+/+) mice were fed a low Selenium diet (0 mg/kg), they too exhibited altered synaptic transmission and synaptic plasticity. Our observations suggest an important role for both selenoprotein P and dietary selenium in overall proper synaptic function.

Fc-RAP: Reelin molecules have recently been discovered to form higher-order complexes in vitro and in vivo. This observation was further refined by showing that reelin is secreted in vivo as a disulfide-linked homodimer. Deletion of a short region, called the CR-50 epitope, located at the N-terminus of the molecule abolishes oligomerization. This mutated reelin fails to efficiently induce Dab1 phosphorylation in primary mouse neurons.

These results are in accordance with earlier observations that an antibody against the CR-50 epitope antagonizes reelin function in vitro and in vivo. Clustering of ApoER2 and/or VLDLR induces Dab1 phosphorylation and downstream events including activation of SFKs and modulation of PKB/Akt. Furthermore, modulation of long-term potentiation (LTP), one of the biological effects of reelin, is also mimicked by reelin-independent receptor clustering. These findings strongly suggest that receptor-induced dimerization or oligomerization is sufficient for Dab1 tyrosine phosphorylation and downstream signaling events without the need for an additional co-receptor providing tyrosine kinase activity.

As shown herein, Reelin plays an active role in the processes of synaptic plasticity and learning. The invention also includes the identification and use of mechanisms for Reelin protein processing to enhance and/or repair cognitive function. For example, it is disclosed herein that: contextual fear learning and theta burst stimulation (tb-stim) cause changes in Reelin processing; the metalloproteinases, tPA and MMP-9 are differentially involved in Reelin processing during synaptic plasticity and learning; supplementation of Reelin fragment complement can enhance associative and spatial learning and memory; and reelin fragments associate with Aβ plaques, its expression and processing is altered by AD-related mutations, and Reelin supplementation can overcome the LTP deficits found in the Tg2576 AD mouse model.

Reelin-Induced Enhancement of Long-Term Potentiation in Acute Hippocampal Slices.

Figure 1:
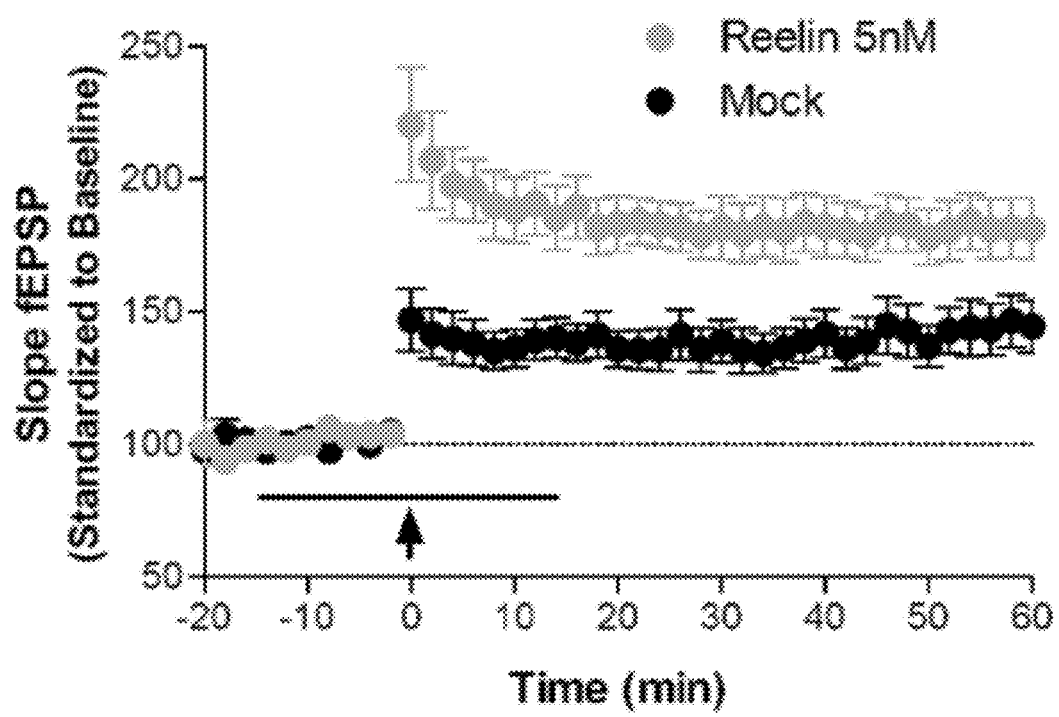
FIG. 1. Application of recombinant Reelin enhances LTP. Field recordings from acute hippocampal slices in area CAL Wild-type mice were perfused with either 5 nM reelin (n=7) or Mock (n=6).

Reelin is a naturally occurring, secreted protein produced by interneurons of the hippocampus and cortex. Knockout (KO) mice of both reelin receptors, ApoER2 and VLDLR show deficits in long-term potentiation (LTP) in the stratum radiatum of the hippocampus. To verify the absence of reelin signaling underlies this deficit, the inventors performed a simple experiment consisting of the perfusion of purified reelin protein onto wild-type hippocampal slices. As shown in FIG. 1, reelin application enhanced HFS-LTP induced in the stratum radiatum.

Post-Synaptic Mechanisms of Reelin Enhancement of NMDAR Currents.

Figure 2:
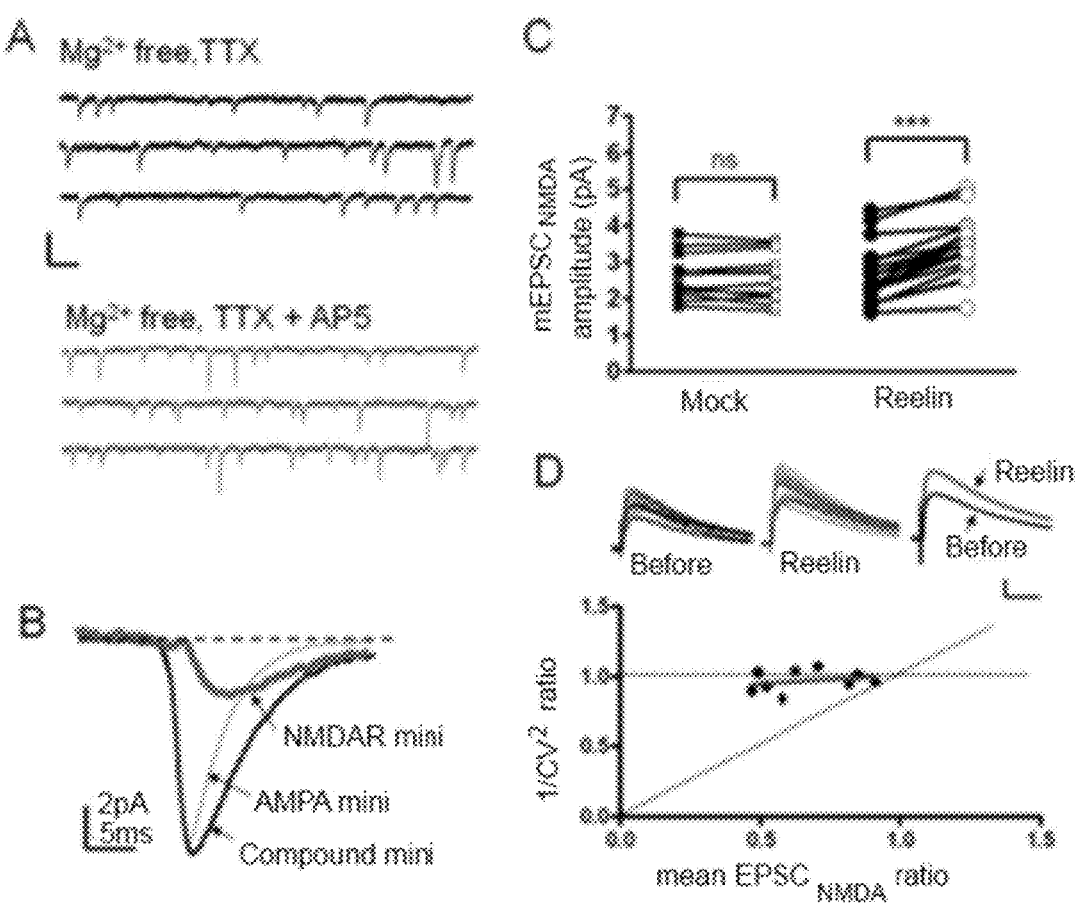
FIG. 2. Reelin enhances NMDAR currents through postsynaptic mechanisms. (A,B) Illustration of measurement of EPSCNMDA. The thick gray trace in B) represents the mEPSCNMDA. C) Reelin treatment significantly increased mEPSCNMDA amplitude (closed circle, before reelin; open circle, after reelin; ***p<0.001; n=18; paired t test). Treatment with mock was without effect [closed square, before mock; open square, after mock; not significant (ns), p>0.05.

Reelin also demonstrates the ability to potentiate CA1 glutamatergic responses. The inventors have recently shown that ApoER2 is present post-synaptically and forms a functional complex with NMDARs in CA1 (4). The derivation of mEPSCNMDA is illustrated in FIG. 2. Cells treated with mock had miniature excitatory post-synaptic current due to NMDA receptors (mEPSCNMDA) that were not significantly changed compared with that before mock treatment ($p>0.05$). Treatment with Reelin was found to significantly increase mEPSCNMDA amplitude ($p<0.001$).

To further verify that synaptic NMDAR response was increased as a result of postsynaptic effects of Reelin, the inventors analyzed the coefficient of variation (CV) of synaptically-evoked NMDAR whole-cell current. When $1/CV^2$ ratios were plotted versus mean EPSCNMDA ratios before and after a 30 minute reelin application in nine experiments, no correlation was established (FIG. 2D). However, the $1/CV^2$ ratios remain relatively unchanged across varying mean EPSCNMDA ratios, confirming reelin activation through a postsynaptic mechanism in CA1 to enhance NMDAR activity.

Differential effects of Reelin treatment on surface levels of AMPAR and NMDAR subunits.

Chronic Reelin treatment can result in the increased AMPA component of synaptic response, alteration of EPSCNMDA kinetics and ifenprodil sensitivity. The inventors sought to determine whether the protein expression levels of AMPAR and NMDAR subunits were changed by Reelin in CA1. Both total and surface levels of GluR1, NR1, NR2A, and NR2B were probed by Western blotting. The inventors first examined whether GluR1, an AMPAR subunit that is increasingly expressed during developmental maturation and subjected to regulate trafficking during synaptic plasticity, was increased on CA1 cell surfaces.

FIG. 3 shows that reelin treatment significantly increased levels of surface GluR1 compared with mock-treated groups, indicating regulated expression and surface insertion via increased mEPSC$_{AMPA}$ and AMPA/NMDA current ratio after chronic Reelin treatment. No changes of either surface or total NR1 levels were observed. In comparison, both total and surface NR2A expression levels were significantly increased after reelin treatment versus mock treatment. Moreover, both total and surface NR2B protein levels were significantly decreased following reelin treatment. Mock treatment had no effect on different glutamate receptor subunit levels compared with non-treated control groups.

Reelin Signaling Translates from a Role in Synaptic Plasticity to Learning and Memory.

Reelin heterozygotes show deficits in both synaptic plasticity and cognitive function. An approximate 50% reduction of Reelin expression results in deficits in both synaptic plasticity and cognitive function (Qiu, S., K. M. Korwek, A. R. Pratt-Davis, M. Peters, M. Y. Bergman, and E. J. Weeber. 2006. Cognitive disruption and altered hippocampus synaptic function in Reelin haploinsufficient mice. *Neurobiol Learn Mem* 85:228-242). Furthermore, bilateral infusion of the lipoprotein antagonist RAP (receptor associated protein), which effectively blocks Reelin binding to its receptors dramatically, reduced associative learning (FIGS. 4A-4D). These results demonstrate a requirement for Reelin for normal memory formation and raise the interesting question of whether increasing Reelin signaling can enhance memory.

The effect of Reelin deficiency on synaptic function is contrasted when Reelin concentrations are enhanced. Direct bilateral ventricle infusion of recombinant Reelin fragment compliment 3 hours prior to associative fear conditioning training enhanced memory formation when tested 24 hours after training in 3-4 month-old wild-type mice (FIG. 4A).

Furthermore, a single injection of Reelin into the ventricles improved spatial learning in the hidden platform water maze (FIG. 4B). Mice that were retrained to find a different platform location (opposite) on day 6 continued to show increased learning ability compared to saline injected mice. Mice receiving a single Reelin injection 5 days prior to training show a lower latency to find the platform on day one. A closer examination shows that the latency to find the platform is significantly reduced after a single exposure to the training paradigm (FIG. 4C). Mice that were retrained to find a different platform location continued to show differences between reelin and saline injections. Swim speeds and all other measurements of activity between treated and non-treated animals remained the same. This data dramatically illustrate the ability of Reelin to modulate in vivo learning and memory formation and the importance of research aimed to identify the mechanisms controlling Reelin protein processing and how the fragments subsequently modulate cognitive function.

Reelin Supplementation Overcame Aβ-Dependent Changes in Synaptic Plasticity.

Reelin signaling is involved in a variety of physiologic changes to the excitatory synapse, as well as normal mammalian cognitive function. Reelin metabolism is altered in three mouse models for AD (PS1-FAD, SweAPPxPS1, and Tg2576) (FIG. 5A). These changes in Reelin fragment complement appear to be correlated with alterations in downstream Reelin signaling, as phosphorylation of the major downstream component, Dab-1, is increased in the SweAPPXPS1 and PSI-FAD, and significantly decreased in the single SweAPP (Tg2576) mouse (FIG. 5B). These data suggest that Reelin metabolism is particularly sensitive to changes in APP processing and/or Aβ accumulation.

The alteration in Reelin fragment complement and Dab-1 phosphorylation in the Tg2576 mice may represent a compromised Reelin signaling system, a phenomenon that if true could be responsible for the synaptic plasticity deficits reported in these mice (Mitchell, J. C., B. B. Ariff, D. M. Yates, K. F. Lau, M. S. Perkinton, B. Rogelj, J. D. Stephenson, C. C. Miller, and D. M. McLoughlin. 2009. X11beta rescues memory and long-term potentiation deficits in Alzheimer's disease APPswe Tg2576 mice. *Hum Mol Genet* 18:4492-4500; Kotilinek, L. A., M. A. Westerman, Q. Wang, K. Panizzon, G. P. Lim, A. Simonyi, S. Lesne, A. Falinska, L. H. Younkin, S. G. Younkin, M. Rowan, J. Cleary, R. A. Wallis, G. Y. Sun, G. Cole, S. Frautschy, R. Anwyl, and K. H. Ashe. 2008. Cyclooxygenase-2 inhibition improves amyloid-beta-mediated suppression of memory and synaptic plasticity. *Brain* 131:651-664; Jacobsen, J. S., C. C. Wu, J. M. Redwine, T. A. Comery, R. Arias, M. Bowlby, R. Martone, J. H. Morrison, M. N. Pangalos, P. H. Reinhart, and F. E. Bloom. 2006. Early-onset behavioral and synaptic deficits in a mouse model of Alzheimer's disease. *Proc Natl Acad Sci USA* 103: 5161-5166). Acute hippocampal slices from 8 month-old Tg2576 mice were perfused with 5 nM recombinant Reelin fragment complement. The inventors find that the Reelin application rescues the LTP defect in aged Tg2576 mice (FIG. 5C) suggesting that the biochemical and structural machinery involved in Reelin signaling downstream of Reelin protein processing is intact in these mice. Furthermore, it is important to note that normal levels of synaptic plasticity are obtainable in this mouse model. Reelin fragments are also associated with dense core plaques in aged (15 month-old) Tg2576 mice (FIG. 5D). As shown in FIG. 6, reelin and related lipoprotein receptor agonists can rescue deficits in synaptic plasticity and cognitive function that result from Aβ accumulation and/or plaque pathology. Reelin rescued the LTP deficit in 12 month-old mice modeled for AD (Tg2576) (FIG. 6).

These data are supported by Reelin associated with Aβ-containing plaques detected in the hippocampus of aged wild-type mice (Madhusudan, A., C. Sidler, and I. Knuesel. 2009. Accumulation of reelin-positive plaques is accompanied by a decline in basal forebrain projection neurons during normal aging. *Eur J Neurosci* 30:1064-1076; Knuesel, I., M. Nyffeler, C. Mormede, M. Muhia, U. Meyer, S. Pietropaolo, B. K. Yee, C. R. Pryce, F. M. LaFerla, A. Marighetto, and J. Feldon. 2009. Age-related accumulation of Reelin in amyloid like deposits. *Neurobiol Aging* 30:697-716). In light of the established role for Reelin in synaptic function, changes in the integrity of Reelin metabolism and signaling plays a profound role in the learning and memory changes previously established in AD mouse models.

Other ligands of lipoprotein receptors have an effect on synaptic function.

Selenium containing Selenoprotein P (SeP) has been identified as another ligand for the lipoprotein receptor ApoER2. SEP has been shown to associate with ApoER2 in the testis and in the CNS. SeP KO mice showed various pathologies, including deficits in hippocampal-dependent LTP and cognitive function (FIG. 7).

Interestingly, the LTP defect in SeP (−/−) mice can be rescued with purified SeP protein supplementation (FIG. 8). Taken together, these data suggest that SeP has a similar role to Reelin by signaling through ApoER2. It is unclear whether SeP can promote receptor clustering or compete with Reelin. However, it appears that SeP is using the ApoER2 as a receptor to internalize the SeP and deliver selenium to the neuron.

Receptor Associated Protein (RAP) is an intracellular protein that can bind with very high affinity to the family of lipoprotein receptors. The Fc-RAP fusion protein is an engineered protein consisting of two RAP molecules connected to form a rough 'dumb bell' shape using the Fc region of an antibody. Instead of binding to and inhibiting ApoER2 and VLDLR, the Fc-RAP can cause receptor clustering and ApoER2 activation. The addition of Fc-RAP has the identical effect as reelin application by increasing LTP induction (FIG. 9). The main difference is that the Fc-RAP is likely to bind all lipoprotein receptors, but only clusters ApoER2 and VLDLR.

Reelin fragment complement in the hippocampus is altered following in vivo memory formation and ex-vivo stimulation.

Reelin is cleaved at specific sites resulting in a stable pattern of Reelin fragments easily quantified by Western blot analysis. These fragments represent potential signaling molecules with properties unique from full-length Reelin. Recombinant Reelin purified from stably transfected HEK293 cells contains fragments of the same size as the major fragments found in the hippocampus. Application of recombinant Reelin fragment compliment can (1) increase synaptic transmission by facilitating AMPA receptor insertion and increasing NMDA receptor function, (2) reduce silent synapses, (3) modify synaptic morphology and (4) enhance LTP (Qiu, S., and E. J. Weeber. 2007. Reelin signaling facilitates maturation of CA1 glutamatergic synapses. *J Neurophysiol* 97:2312-2321; Qiu, S., K. M. Korwek, A. R. Pratt-Davis, M. Peters, M. Y. Bergman, and E. J. Weeber. 2006. Cognitive disruption and altered hippocampus synaptic function in Reelin haploinsufficient mice. *Neurobiol Learn Mem* 85:228-242).

Additionally, fear conditioned learning produces changes in the endogenous Reelin fragment complement. The inventors found a dramatic change in Reelin expression and fragment complement over the 18 hours following contextual fear conditioning, particularly in the 450 and 180 kDa fragments (FIG. 10).

Moreover, theta burst stimulation delivered to the Schaffer collateral pathway led to significant increases in Reelin expression and fragment cleavage at 15 minutes post-stimulation (FIG. 10). These results show that integration and control of Reelin signaling responsible for alterations in synaptic plasticity and modulation of learning and memory involves the processing of Reelin into functionally-distinct fragments.

The inventors also found that the efficacy of generating the 370 kDa product to be partially dependent on a candidate Reelin-cleaving enzyme, tPA. This potential mechanism of regulation has profound implications on how this signaling system is integrated into known mechanisms of neuronal regulation and coordinated to participate in physiological processes such as learning and memory.

MMP-9- and tPA-Mediated Reelin Processing.

Recently it was shown that the processing of Reelin by metalloproteinase(s) is essential for normal cortical plate formation (Jossin, Y., and A. M. Goffinet. 2007. Reelin signals through phosphatidylinositol 3-kinase and Akt to control cortical development and through mTor to regulate dendritic growth. *Mol Cell Biol* 27:7113-7124), though the specific enzyme responsible remains as yet unknown. This discovery suggests that metalloproteinase-mediated Reelin processing may be important for directed Reelin signaling in the adult brain as well. Both tPA and MMP-9 are candidate metalloproteinases with clearly demonstrated roles in regulating synaptic plasticity and cognitive function (Bozdagi, O., V. Nagy, K. T. Kwei, and G. W. Huntley. 2007. In vivo roles for matrix metalloproteinase-9 in mature hippocampal synaptic physiology and plasticity. *J Neurophysiol* 98:334-344; Nagy, V., O. Bozdagi, A. Matynia, M. Balcerzyk, P. Okulski, J. Dzwonek, R. M. Costa, A. J. Silva, L. Kaczmarek, and G. W. Huntley. 2006. Matrix metalloproteinase-9 is required for hippocampal late-phase long-term potentiation and memory. *J Neurosci* 26:1923-1934; Huang, Y. Y., M. E. Bach, H. P. Lipp, M. Zhuo, D. P. Wolfer, R. D. Hawkins, L. Schoonjans, E. R. Kandel, J. M. Godfraind, R. Mulligan, D. Collen, and P. Carmeliet. 1996. Mice lacking the gene encoding tissue-type plasminogen activator show a selective interference with late-phase longterm potentiation in both Schaffer collateral and mossy fiber pathways. *Proc Natl Acad Sci USA* 93:8699-8704; Pang, P. T., and B. Lu. 2004. Regulation of late-phase LTP and long-term memory in normal and aging hippocampus: role of secreted proteins tPA and BDNF. *Ageing Res Rev* 3:407-430; Zhuo, M., D. M. Holtzman, Y. Li, H. Osaka, J. DeMaro, M. Jacquin, and G. Bu. 2000. Role of tissue plasminogen activator receptor LRP in hippocampal long-term potentiation. *J Neurosci* 20:542-549; Baranes, D., D. Lederfein, Y. Y. Huang, M. Chen, C. H. Bailey, and E. R. Kandel. 1998. Tissue plasminogen activator contributes to the late phase of LTP and to synaptic growth in the hippocampal mossy fiber pathway. *Neuron* 21:813-825).

Reelin is processed by both tPA and MMP-9 to generate the major Reelin fragment products found in vivo (FIG. 12A, 12B). As it can be seen, tPA increases the 370 kDa (N-R6) and 80 kDa (R7-8) fragments under cell free conditions (FIG. 12A), indicating that tPA cleaves Reelin between R6-R7 (FIG. 13). Cleavage of Reelin by Plasmin results in a spectrum of products of previously unknown identity and specific retention of the 180 kDa fragment. Application of recombinant tPA to primary neurons resulted in a complete conversion of extracellular Reelin from full-length to the 370 and 180 kDa forms, and a decrease in intracellular 180 kDa Reelin. Furthermore, MMP-9 increases both the 370 kDa (N-R6) and 180 kDa (N-R2) fragments, as well as a fragment found just below the well known 180 kDa fragment (FIG. 12B). These results under cell free conditions support that MMP-9 can cleave Reelin at both cleavage sites, R2-3 and R6-7; however, application of MMP-9 to primary neurons led to a specific accumulation of the 180 kDa fragment in cells and MMP-9 inhibition for 24 hours led to a dramatic increase in full-length cellular Reelin and decrease in cellular 180 kDa Reelin. These results suggest that under normal conditions, MMP-9 is responsible for cleaving Reelin between R2-R3 (See fragment map; FIG. 13). Taken together, these preliminary data suggest that MMP-9 and tPA are sufficient for generation of the major Reelin fragments found in vivo.

As shown above, reelin protein processing in the hippocampus is susceptible to in vitro and in vivo synaptic activity. It also appears that MMP-9 and tPA are involved in the process of Reelin metabolism. Surprisingly, a single exogenous Reelin application enhances learning and memory for at least eleven days in adult wild-type mice. When considering the role of lipoprotein receptors in Aβ clearance, and the identification of Reelin association to Aβ plaques in an AD mouse model, the question of the role of Reelin in the etiology and pathogenesis of AD becomes a timely and important area of research. Moreover, the now improved understanding of the mechanisms and implications of Reelin processing provides, inter alia, AD therapeutic interventions aimed toward removal of Aβ and improvement of cognitive function.

Moreover, all that is known regarding Reelin localization in the adult brain has been generated using an antibody that recognizes the N-R2 region. The N-R2 region is present in the full-length (N-R8), N-R2 and N-R6 fragments of Reelin, but not in the other major fragments. Therefore, the 3-epitope mapping approach ((FIG. 13) affords unprecedented spatial resolution to monitor changes in Reelin product production and localization.

In order to characterize specific fragments produced by tPA- and MMP-9-dependent Reelin processing in the context of normal synaptic function and memory formation, the inventors generated cleavage-resistant Reelin mutant constructs using site-directed mutagenesis FIG. 14). Reelin mutants include constructs resistant to cleavage (Rln-Res) by tPA at R2-3, to MMP-9 at R6-7 and to both enzymes at R2-3 and R6-7. Fragments mimicking cleavage by tPA or MMP-9 with, or without a cleavage resistant site are also contemplated. One complementary Reelin construct is tagged in an identical fashion as the Rln-Res protein; however, it does not contain the two altered sites for cleavage (Reelin cleavage labile; FIG. 14)). A tagged fragment produced with both sites mutated (negative control construct) and a tagged R3-6 fragment shown to bind ApoER2 and VLDLR (potential positive control) is included. The Reelin constructs are sub-cloned into mammalian expression vectors containing N-terminal polyhistidine tags and/or C-terminal Myc tags to allow later recognition of exogenous Reelin. The exact cleavage sites can be identified by using purified full-length Reelin reacted with either tPA or MMP-9 therefore the resultant fragments can be isolated.

Reelin Application Recovers Spine Density in HRM and Reelin-Null Mice

In cultured hippocampal neurons, reelin signaling is required for normal development of dendritic structures. In the absence of reelin or the intracellular adaptor protein Dab1, neurons exhibit stunted dendritic growth and a reduction in dendritic branches, a phenotype analogous to that seen in neurons lacking the reelin receptors apoER2 and VLDLR (Niu S, Renfro A, Quattrocchi C C, Sheldon M, D'Arcangelo G. Reelin promotes hippocampal dendrite development through the VLDLR/ApoER2-Dab1 pathway. Neuron 2004; 41:71-84). The HRM exhibits a deficit in hippocampal-dependent contextual fear conditioned learning and synaptic plasticity in area CA1 of the hippocampus. It is believed that these behavioral and physiologic phenotypes of the HRM are due in part to reduced or inhibited synaptic connectivity. This is supported by the observation that HRM have a reduction in spine density (FIG. 15).

Dendritic spines are small protrusions that cover the surface of dendrites and bear the postsynaptic structures that form excitatory synapses. Abnormal shapes or reduced numbers of dendritic spines are found in a number of cognitive diseases, such as Fragile X syndrome, William's syndrome, Rett syndrome, Down's syndrome, Angelman syndrome and autism. A reduction in the number of dendritic spines suggests that a constitutive level of reelin/lipoprotein receptor-mediated signaling is required for development of dendritic structures, which are crucial for intensive information processing by the neurons. This notion is in agreement with studies showing that heterozygote reeler mice exhibit reduced dendritic spine densities and impaired performance in certain learning and memory behaviors.

Hippocampal neurons cultured from reeler embryos had significantly less dendritic spines, a phenotype that can be rescued by addition of exogenous recombinant reelin to the culture. Organotypic hippocampus cultures were created from 6-7 day-old wild-type, HRM and Reelin-deficient mice and treated with 5 nm Reelin for 21 days. Fluorescent dye was injected into neuronal cells by administering whole cell patch clamp current and the cells were visualized under the confocal microscope after fixation. Reelin-treated of HRM cells showed an increase in dendritic spine density after 21 days compared to age matched neurons from wild-type culture (FIG. 15B). In contrast, mock (conditioned media from non-stably transfected cells) application showed no change in spine density (FIG. 15C). The same experiment in reelin knockout mice showed that reelin application also rescued the dendritic spine density compared to mock controls (FIGS. 15C and 15F). Both the reelin treated cells resembled the dendritic spine morphology seen in WT cells (FIG. 15D) and when quantified, dendritic spines significantly increased in reelin-treated HRM cultures compared to mock treated controls and are similar to spine density levels observed in wild-type cultures (FIG. 15A).

Treatment of organotypic cultures consisted of repeated 5 nM Reelin application every 3 days for 21 days. To verify that this application protocol represented a chronic application of reelin, and reelin was not being degraded or actively removed from the media, the inventors removed 15 ul of media from culture plates at times of 0, 6, 12, 24, 48, 72, and 96 hours following reelin application. Western analysis of these aliquots showed no degradation or reduction in Reelin (FIG. 15G). Thus, the increase in spine density is due to reelin present at physiologic relevant levels for the entire 21 day application.

In Vivo Reelin Application Effects on Overall Behavioral Responses.

Mice lacking reelin exhibit abnormal lamination of neuronal layers, which is most severely seen in the cortex, cerebellum, and hippocampus. The Reelin knockout exhibits the "reeler" phenotype, characterized by rest tremor and ataxia.

Although the Cajal-Retzius cells eventually degenerate after the completion of development, reelin continues to be expressed by GABAergic interneurons in the cortex and hippocampus. In the adult, as in the developing brain, Reelin's molecular effects are mediated through two receptors: the very low density lipoprotein receptor (VLDLR) and the apoliporotein E receptor 2 (ApoER2). Reelin-dependent signaling through ApoER2 and VLDLR occurs through hetero- or homo-dimerization of receptors and can activate the CDK-5 and PI3-K signal transduction pathways. Reelin signaling is also linked to modulation of synaptic plasticity and memory formation.

The heterozygote reelin mouse (HRM) exhibits haploinsufficiency and a 50% reduction in reelin protein levels, but does not lead to an overt "reeler" phenotype. Instead, Reelin haploinsufficiency manifests as very subtle neuroanatomical, physiologic and behavioral deficits. These include a decrease in dendritic spines in the parietal-frontal cortex (PFC) pyramidal neurons in addition to basal dendritic cells of hippocampal CA1 pyramidal neurons and cortical neuropil hypoplasia. The HRM displays a reduced density of nicotinamide-adenine dinucleotide phosphate-diaphorase (NADPH-d)-positive neurons in the cortical gray matter, altered dopaminergic markers in the mesotelencephalic dopamine pathway. The HRM shows impaired short-term and long-term plasticity in hippocampal CA1 synapses. Long-term potentiation (LTP) is disrupted using both high frequency stimulation and pairing stimulation protocols. Behaviorally, the HRM exhibits an age-dependent decrease in prepulse inhibition.

The HRM has often been referred to as a possible mouse model for human schizophrenia. Reelin mRNA and protein levels are reduced in post-mortem brains of schizophrenic patients resulting in approximately 50% of that found in normal control post mortem brains. Investigation of the Reeler heterozygote found other similarities to the human condition, including: decreased GAD67 expression, decreased tactile and acoustic prepulse inhibition, and reduced spine density. Schizophrenia is also associated with severe cognitive impairment and disordered thinking. This manifests as a lack of overall attention, impairment of information processing disrupting both declarative and non-declarative memories. Importantly, HRM show a similar cognitive dysfunction, observed as reduced associative fear conditioned learning.

An HRM breeding pair (B6C3Fe a/a-Reln$^{rl}$/+ strain) was obtained from the Jackson Laboratory. The offspring of both HRM were genotyped by using genomic DNA from a 2 mm diameter earpunch. The primer sequences were, forward: 5'-taatctgtcctcactctgcc-3' (SEQ ID NO:1); reverse: 5'-acagt-tgacataccttaatc-3'(SEQ ID NO:2); reverse mutated: 5'-tgcat-taatgtgcagtgttgtc-3'(SEQ ID NO:3). Animal care and use protocol was approved by the Institutional Animal Care and Use Committee of Vanderbilt University.

The culmination of research on Reelin's actions in developing CNS and adult cognitive processes raises the question of whether the cognitive deficits in HRM are due to reelin haploinsufficiency, leading to a decrease in signal transduction and LTP formation, or reduction in dendritic spines, resulting in decreased information processing and storage in areas involved in learning and memory. Alternatively, HRM show reduced spine density, thus, these deficits may be due to developmental defects that result in the mis-wiring of critical regions of the CNS.

The increase in sEPSCs in wild-type mice, but not in Reelin knockout mice despite chronic reelin exposure indicated that spine formation was not the sole factor influencing spontaneous synaptic activity in cultured neurons. This would suggest that developmental abnormalities resulting in altered synaptic connectivity in the hippocampus of HRM, and to a greater extent in the Reelin-deficient mice, were the underlying basis for the cognitive deficits in the HRM.

The HRM and wild-type mice are similar for open field and elevated plus maze. These behavioral tests are essential for evaluation and proper determination of associative fear conditioning results. In addition, the open field and elevated plus maze tasks allow assessment of any differences in locomotor activity or anxiety after the cannulation placement and injection.

For the open field tests, general locomotor activity was measured using the open field task. Animals were placed in the open field (27×27 cm) chamber for 15 min in standard room-lighting conditions. Activity in the open field was monitored by 16 photoreceptor beams on each side of the chamber and analyzed by a computer-operated (Med Associates) animal activity system.

For the elevated plus maze experiments, mice were placed in the elevated plus maze one hour after they had completed the open field task to test their levels of anxiety. The apparatus consisted of two opposing open arms (30 cm×5 cm) and two opposing closed arms (30 cm×5 cm×15 cm) connected by a central square platform and was 40 cm above the ground. Testing took place under standard-lighting conditions. Mice were placed in the open arms facing the closed arms at the beginning of the 5 minute session. The number of entries and the total time spent in the open arms were recorded.

Bilateral intracerebroventricular cannulations on HRM mice were followed by evaluating open field and elevated plus maze tests. Following a 5 day recovery period from the surgical procedure, these mice were injected with 1 ul of either mock or reelin through two PESO tubes attached to two Hamilton syringes. Mice were visually assessed daily for overall health following surgery. All mice used for these studies showed no signs of infection assessed by visual inspection of the site of incision and rectal temperature monitored daily.

The injection of 1 ul of a concentrated Reelin solution represented a final distributed concentration of 5 nM. To test for dispersion of Reelin cannulated wild type mice were injected monolateral with 1 ul Reelin and sacrificed 1 hour following injection. Brains were fixed and immunohistochemical analysis for Reelin was performed. No discernable distribution of Reelin was seen in the Reelin injected hemisphere, however, an increase in overall Reelin immunoreactivity was observed in the treated versus non treated hemispheres. This suggests that Reelin quickly diffuses from the ventricle by the time of behavioral testing.

One hour after Reelin injection the experimental mice were placed in the open field chamber and distance traveled over a 15 minute period was measured. Immediately following the open field task, mice were placed in the elevated plus maze and the number of entries and percent time in the open arms were measured. A greater amount of time spent in the closed arms compared to the open arms is an index of higher anxiety. No differences were seen between the mock and reelin treated heterozygote mice in these two tasks (FIG. 16A-B).

Mice normally exhibit a startle response to loud noise but if a moderate noise is presented prior to the loud noise, the startle response is attenuated, an effect known as prepulse inhibition (PPI). PPI represents another compelling behavioral phenotype of the HRM that recapitulates human schizophrenia. PPI was performed one hour after elevated plus maze. The mouse was placed in a Plexiglas cylinder in a dark PPI chamber (Med Associated Inc.; St. Albans, Vt.) with the presence of background noise provided by a fan. After mice were allowed to acclimate for 5 minutes in the chamber, they were underwent a random presentation of five stimulus trial types: 120 db stimulus startle alone, and each of a 70, 76, 82, and 88 db prepulse followed by a 120 db startle for a total of 9 trials per type. The percent prepulse inhibition and the peak startle were measured using the Startle Reflex 5 software.

The inventors have previously shown that the HRM show a deficit in PPI, specifically at the 82 dB prepulse. To determine whether Reelin rescues this deficit, the inventors performed PPI in Reelin-injected cannulated mice. Following the elevated plus maze, mice were placed in the startle reflex chamber and given a random presentation of 5 trial types: no prepulse with a 120 dB acoustic startle, or 70, 76, 82, 88 dB prepulses with a 120 dB acoustic startle. The inventors saw that there was no difference in the startle to acoustic stimulation, where no prepulse was presented with a 120 dB acoustic startle between the mock treated and reelin treated HRM (FIG. 16D). Additionally, there was no difference in the PPI between both treatment groups at any of the prepulse levels (FIG. 16C).

The HRM shows a deficit in associative learning when compared to their wild-type littermates. Contextual fear conditioning was performed on Reelin and Mock-treated HRM at 5 hours post-injection to assess whether Reelin haploinsufficiency is responsible for this change rather than permanent developmental defects. Fear conditioning was performed 2 hours after PPI. The conditioning chamber (26×22×18 cm; San Diego Instruments, San Diego, Calif.) was made of Plexiglas and was equipped with a grid floor for delivery of the unconditioned stimulus (US) and photobeams to monitor activity. The conditioning chamber was placed inside a soundproof isolation cubicle.

Training occurred in the presence of white light and background noise generated by a small fan. Each mouse was placed inside the conditioning chamber for 2 minutes before the onset of a conditioned stimulus (CS), an 85 dB tone, which lasted for 30 seconds. A 2 sec US foot-shock (0.5 mA) was delivered immediately after the termination of the CS. Each mouse remained in the chamber for an additional 60 seconds, followed by another CS-US pairing. Each mouse was returned to its home cage after another 30 seconds. The test for contextual fear memory was performed 1, 24, and 72 hours after training by measuring freezing behavior during a 3 minute test in the conditioning chamber.

Freezing was defined as lack of movement in each 2 second interval. Cued fear memory was tested in the presence of red light, vanilla odor, and the absence of background noise. The grid floor was covered and the walls were covered with alternating black and white plastic panels. Each mouse was placed into this novel context for 3 minutes at 1 hour and 24 hours after training They were exposed to the CS for another 30 min following this. Freezing behavior was recorded and processed by the SDI Photobeam Activity System software throughout each testing session.

Figure 17A:
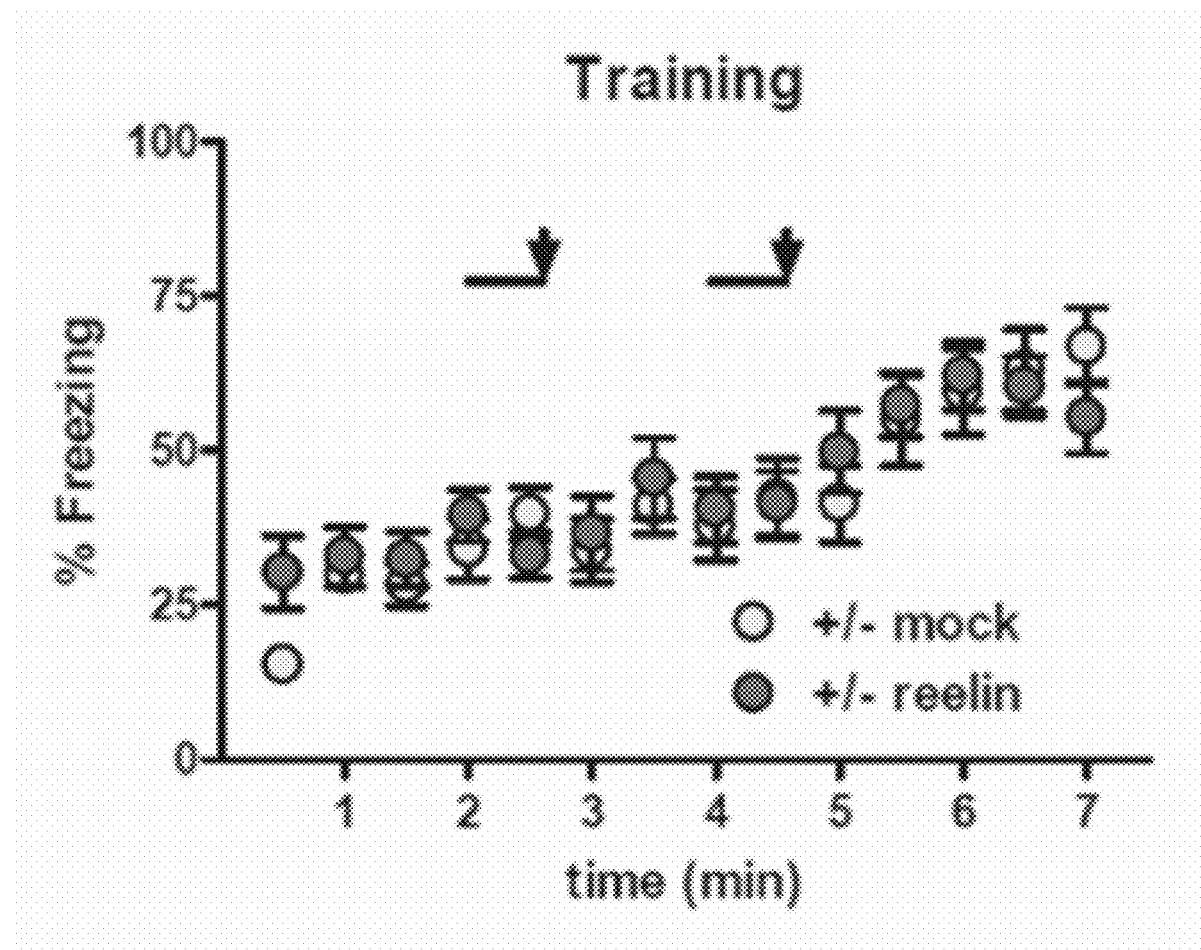

The aversive unconditioned stimulus (US), a 5 mA foot-shock, was paired twice with an auditory tone (conditioned stimulus, CS). During the training period, both animals showed similar levels of freezing after the presentation of the US with an increasing trend of freezing (FIG. 17A). This indicates that the acquisition of the fear memory is similar in both groups and freezing ability is similar. Mice were placed back into the context in which they were trained at 1, 24 or 72 hours following training There was no difference between the Reelin treated mice compared to the mock treated controls at 1 hour post-training (FIG. 17B). However, 24 hours after training, mice were placed into the chamber for the second time to examine the effects of Reelin on long-term memory formation. Reelin-treated mice showed a significant increase in percent freezing compared to mock-treated controls (FIG. 17C). These levels are similar to the levels of freezing in WT mice that the inventors have previously shown (~70%), while the mock-treated controls resembled our HRM. This suggests that reelin rescues the hippocampal-dependent associative learning deficits seen in the HRM to resemble the WT mouse. When tested 72 hour following training, there is no statistical significance between the two treatment groups, although there is trend for an increase in freezing in the Reelin group compared to mock controls (FIG. 17D). This may represent a consolidation effect in some of the mice in that the re-introduction into the context in the absence of the aversive stimulus may lead to the recall and re-organization of the memory. The ensure that both treatment groups had similar sensitivities to the foot-shock, a shock threshold test was performed. No difference was seen between reelin-treated and mock-treated mice (FIG. 17E). Thus, Reelin replacement to the CNS of HRM rescues the contextual fear conditioning defect.

In Vivo Application of Receptor Associated Protein.

The results above show that increasing Reelin, and subsequent Reelin signaling, in the hippocampus rescues the cognitive deficit. If the decrease in ApoER2 and VLDLR signaling is responsible for the cognitive defects in HRM, then one should be able to mimic these behavioral changes by blocking ApoER2 and VLDLR. Receptor Associated Protein (RAP) serves as a molecular chaperone for the family of lipoprotein receptors allowing transport to the plasma membrane without premature binding to ligand. Applied exogenously, RAP binds to the extracellular portion of the lipoprotein receptor and acts as an effective antagonist. Exogenous application of RAP results in association of inserted receptors and can effectively block extracellular ligand-induced signaling. The use of RAP as a biological antagonist has previously been used to block receptor-induced signaling in culture and tissue, and can effectively block long-term potentiation (LTP) in wild-type hippocampus. Thus, the behavioral tests were performed on wild-type mice injected with 1 ul of concentrated GST-RAP or GST as a negative control.

Figure 19A:
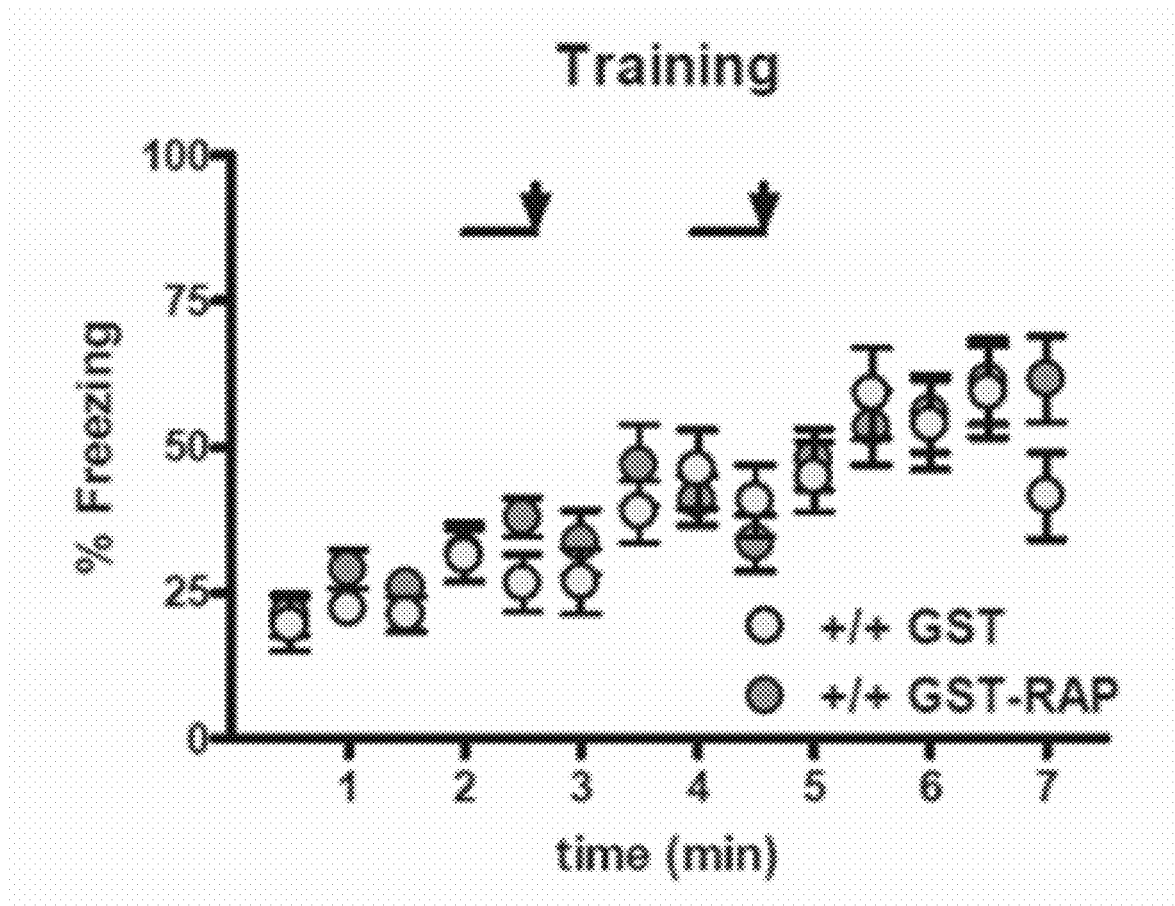
Figure 19B:
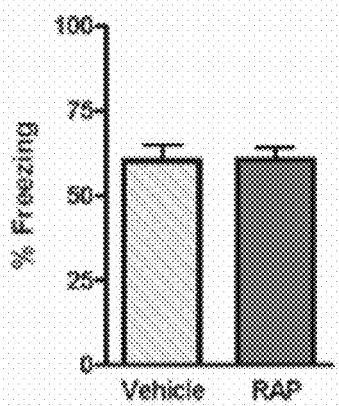
Figure 19C:
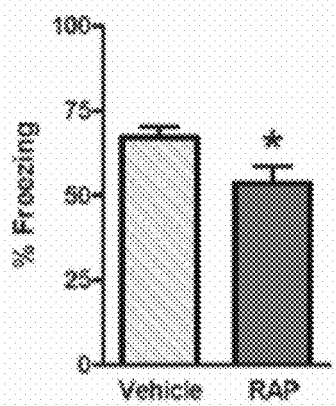
Figure 19D:
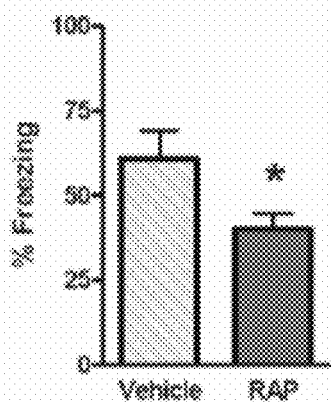
Figure 19E:
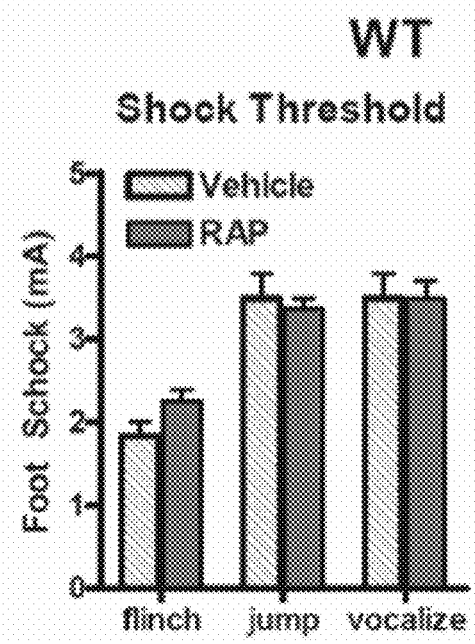

Exogenous GST-RAP or GST (used as a negative control) ha no effect on overall behavior (FIG. 18A-B) and no change was seen in PPI or acoustic startle (FIG. 18C-D). There were no changes in freezing during fear condition experiments or in testing to the context 1 hour after training (FIG. 19A-C). However, GST-RAP injection resulted in a significant decrease in freezing to the context to a level identical to that seen in our HRM Mock treated animals and those levels previously reported in HRM mice (FIG. 19C). No differences were seen in shock thresholds between the two treatment groups (FIG. 19D).

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. A method of improving associative learning and spatial learning and long term potentiation of neurons in a subject, comprising the step of administering a therapeutically effective amount of a 180 kDa Reelin protein fragment or a 370 kDa Reelin protein fragment to the subject;

where the improvement in associative learning and spatial learning is between 20% and 400% improvement and improvement in long term potentiation is between 20% and 46%; and wherein the 180 kDa Reelin protein fragment or the 370 kDa Reelin protein fragment is administered into the ventricles of the subject.

2. The method of claim 1, wherein the therapeutically effective amount of the 180 kDa Reelin protein fragment or the 370 kDa Reelin protein fragment is about 5 nM.

* * * * *

UNITED STATES PATENT AND TRADEMARK OFFICE
CERTIFICATE OF CORRECTION

PATENT NO. : 9,241,975 B2  
APPLICATION NO. : 13/206174  
DATED : January 26, 2016  
INVENTOR(S) : Edwin Weeber, Lisa Zhao and Melinda Peters Page 1 of 1

It is certified that error appears in the above-identified patent and that said Letters Patent is hereby corrected as shown below:

On the Title page, Item (54) Title:
and
In the Specification:

Column 1, line 1, should read:

REELIN RESCUES COGNITIVE FUNCTION

In the Specification:

Column 1, lines 12-17, should read:

GOVERNMENT INTEREST STATEMENT

This invention was made with government support under Grant Number R01 NS043408 awarded by the National Institutes of Health. The government has certain rights in the invention.

Signed and Sealed this
Twenty-sixth Day of April, 2016

Michelle K. Lee
*Director of the United States Patent and Trademark Office*

SEQUENCE LISTING

```
<160> NUMBER OF SEQ ID NOS: 3

<210> SEQ ID NO 1
<211> LENGTH: 20
<212> TYPE: DNA
<213> ORGANISM: artificial sequence
<220> FEATURE:
<223> OTHER INFORMATION: Forward Primer Sequence

<400> SEQUENCE: 1
taatctgtcc tcactctgcc                                               20

<210> SEQ ID NO 2
<211> LENGTH: 20
<212> TYPE: DNA
<213> ORGANISM: artificial sequence
<220> FEATURE:
<223> OTHER INFORMATION: Reverse primer Sequence

<400> SEQUENCE: 2
acagttgaca taccttaatc                                               20

<210> SEQ ID NO 3
<211> LENGTH: 22
<212> TYPE: DNA
<213> ORGANISM: artificial sequence
<220> FEATURE:
<223> OTHER INFORMATION: Reverse mutated primer sequence

<400> SEQUENCE: 3
tgcattaatg tgcagtgttg tc                                            22
```